(12) United States Patent
Wilsher et al.

(10) Patent No.: US 12,019,086 B2
(45) Date of Patent: *Jun. 25, 2024

(54) MULTIPLE CAROUSEL CARTRIDGE-BASED DISPENSING SYSTEM AND METHOD

(71) Applicant: BD KIESTRA B.V., Drachten (NL)

(72) Inventors: Michael John Wilsher, Herts (GB); Simon Jowett, Hertfordshire (GB); Roy Norman Gladwin, Bucks (GB); Mark William Horobin, Hertfordshire (GB); Kenneth Charles Smith, Hertfordshire (GB); Duncan Stevenson, Hertfordshire (GB); Timothy Roy Hansen, Spring Grove, PA (US); Johannes Wijnandus Thiecke, Groningen (NL)

(73) Assignee: BD KIESTRA B.V., Drachten (NL)

( * ) Notice: Subject to any disclaimer, the term of this patent is extended or adjusted under 35 U.S.C. 154(b) by 15 days.

This patent is subject to a terminal disclaimer.

(21) Appl. No.: 17/836,130

(22) Filed: Jun. 9, 2022

(65) Prior Publication Data
US 2022/0404381 A1     Dec. 22, 2022

Related U.S. Application Data

(63) Continuation of application No. 17/298,831, filed as application No. PCT/US2019/064231 on Dec. 3, 2019, now Pat. No. 11,385,249.
(Continued)

(51) Int. Cl.
G01N 35/02    (2006.01)
G01N 35/04    (2006.01)
G01N 35/10    (2006.01)

(52) U.S. Cl.
CPC .......... *G01N 35/025* (2013.01); *G01N 35/04* (2013.01); *G01N 35/1002* (2013.01);
(Continued)

(58) Field of Classification Search
None
See application file for complete search history.

(56) References Cited

U.S. PATENT DOCUMENTS

| 4,301,929 A | 11/1981 | Fitzgerald et al. |
| 4,478,095 A | 10/1984 | Bradley |

(Continued)

FOREIGN PATENT DOCUMENTS

| CN | 101636481 A | 1/2010 |
| CN | 103874759 A | 6/2014 |

(Continued)

OTHER PUBLICATIONS

Office Action from corresponding European Application No. 19892430.0-1001 dated Jan. 5, 2023 (11 pp.).
(Continued)

*Primary Examiner* — P. Kathryn Wright
(74) *Attorney, Agent, or Firm* — Botos Churchill IP Law LLP

(57) ABSTRACT

An improved system and method for the selection and dispensing of reagents onto a target testing medium in an automated laboratory environment. The system utilizes multiple carousels rotatably-mounted upon a central turntable. The position of the central turntable, as well as the rotation of each carousel is controlled by a microprocessor-based control system. Multiple dispensers, each capable of storing and dispensing a particular reagent, are mounted about the circumference of each carousel. This configuration provides much higher reagent density than previously available. The testing medium is positioned at one or more loading stations. The control system directs the central turntable to a position from which a selected one of the carousels can be rotated so as to position a selected dispenser above the testing medium. The selected dispenser is then actuated to release a predetermined reagent onto the testing medium. The system can
(Continued)

be configured so that multiple reagents can be dispensed, each from an associated dispenser, onto a single or multiple testing mediums. Each of these actuated dispensers being positioned over the targeted testing medium(s) positioned at one or more loading stations.

19 Claims, 18 Drawing Sheets

Related U.S. Application Data

(60) Provisional application No. 62/775,030, filed on Dec. 4, 2018.

(52) U.S. Cl.
CPC ............. *G01N 2035/0443* (2013.01); *G01N 2035/0453* (2013.01); *G01N 2035/0455* (2013.01); *G01N 2035/0486* (2013.01); *G01N 2035/0491* (2013.01)

(56) References Cited

U.S. PATENT DOCUMENTS

| | | | |
|---|---|---|---|
| 4,844,868 A | 7/1989 | Rokugawa | |
| 4,849,176 A | 7/1989 | Sakagami | |
| 4,906,433 A | 3/1990 | Minekane | |
| 5,654,200 A | 8/1997 | Copeland et al. | |
| 5,885,530 A | 3/1999 | Babson et al. | |
| 6,071,477 A * | 6/2000 | Auclair | G01N 35/04 |
| | | | 235/375 |
| 7,670,553 B2 | 3/2010 | Babson | |
| 11,385,249 B2 * | 7/2022 | Wilsher | G01N 35/1002 |
| 2002/0164807 A1 * | 11/2002 | Itaya | G01N 35/1065 |
| | | | 422/65 |
| 2004/0191128 A1 | 9/2004 | Bogen et al. | |
| 2005/0123446 A1 | 6/2005 | Yamazaki et al. | |
| 2006/0169719 A1 | 8/2006 | Bui | |
| 2009/0017491 A1 | 1/2009 | Lemme et al. | |
| 2010/0097893 A1 | 4/2010 | Ooi et al. | |
| 2012/0277905 A1 | 11/2012 | Botma et al. | |
| 2014/0273241 A1 | 9/2014 | Ochranek et al. | |
| 2014/0273245 A1 | 9/2014 | Ochranek et al. | |

FOREIGN PATENT DOCUMENTS

| | | |
|---|---|---|
| CN | 205574828 U | 9/2016 |
| EP | 2518136 A1 | 10/2012 |
| JP | H06-230016 A | 8/1994 |
| JP | H11-103849 A | 4/1999 |
| JP | 2010515437 A | 5/2010 |
| JP | 2010533299 A | 10/2010 |
| JP | 2014512822 A | 5/2014 |
| KR | 20150093239 A | 8/2015 |
| WO | 2007116418 A1 | 10/2007 |
| WO | 2008083437 A1 | 7/2008 |
| WO | 2012148273 A1 | 11/2012 |
| WO | 2014149118 A2 | 9/2014 |
| WO | 2018087451 A1 | 5/2018 |

OTHER PUBLICATIONS

International Search Report and Written Opinion for Application No. PCT/US2019/064231 dated Mar. 24, 2020.
Brazilian Office Action issued in corresponding BR application No. BR112021010357-0 dated Aug. 3, 2023.
Japanese Office Action issued in corresponding JP application No. 2021-532099 dated Nov. 7, 2023.
Chinese Office Action issued in corresponding CN application No. 2019800794399 on Feb. 8, 2024.
Search Report issued in CN application No. 2019800794399 on Feb. 8, 2024.

* cited by examiner

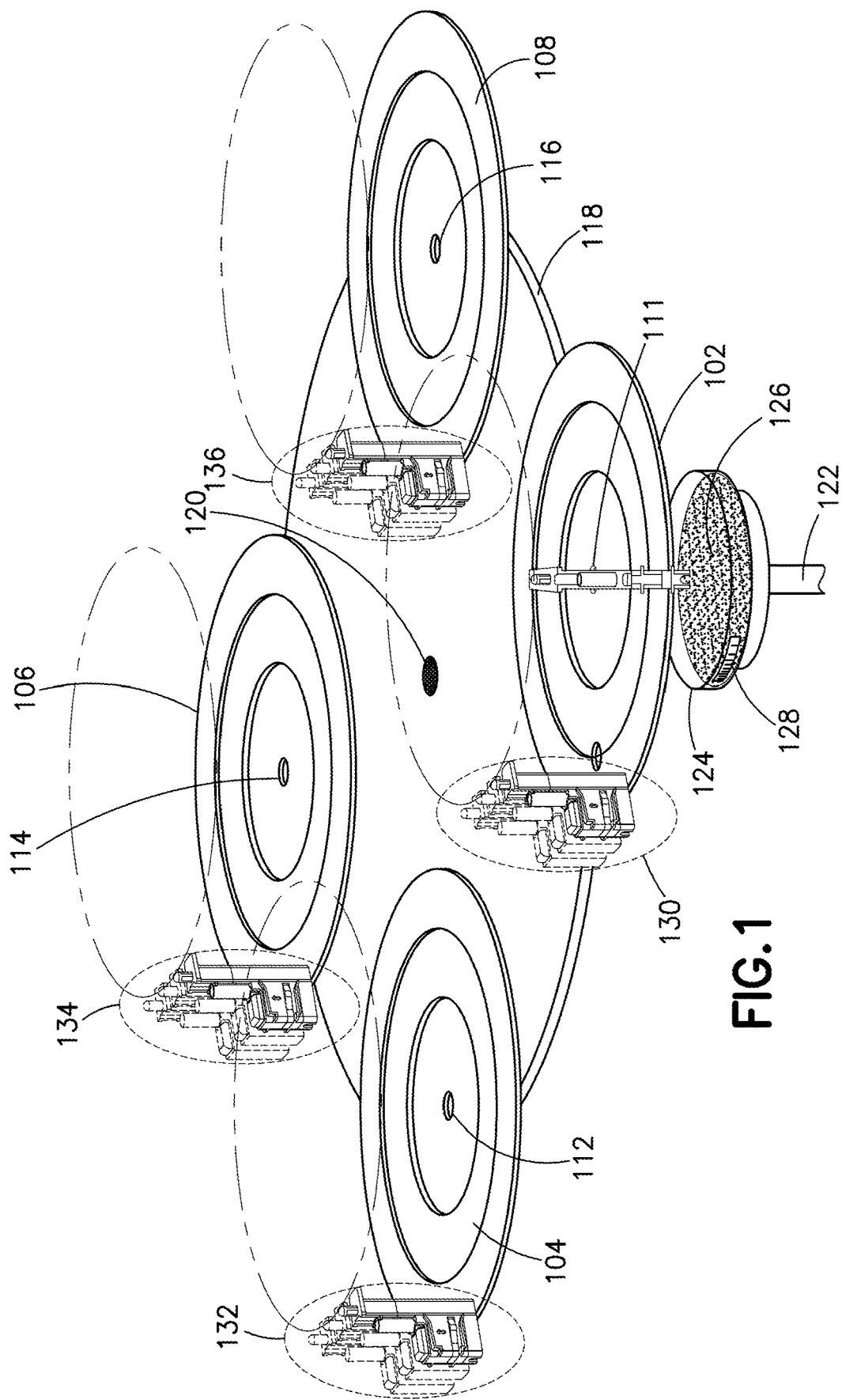

MULTIPLE CAROUSEL CARTRIDGE-BASED DISPENSING SYSTEM AND METHOD

CROSS REFERENCE TO RELATED APPLICATIONS

The present application is a national phase entry under 35 U.S.C. § 371 of International Application No. PCT/US2019/064231, filed Dec. 3, 2019, published as International Publication No. WO 2020/117802 A1, which claims the benefit of the filing date of priority from U.S. Provisional Application No. 62/775,030, filed Dec. 4, 2018, the disclosures of which are hereby incorporated herein by reference.

BACKGROUND OF THE INVENTION

Testing the efficacy of various reagents in an automated laboratory environment requires a system capable of consistently introducing precise measures of one or more selected reagents into one or more designated culture or testing containers (such as plates or petri dishes), and to precise, predetermined locations upon the testing mediums within such containers. For example, systems and methods for automatically dispensing antibiotic discs onto inoculated agar held in petri dishes are known in the art. Such systems typically employ multiple disc dispensers mounted upon a moveable platform, and a specified loading area where a target petri dish is situated. The platform is moved so as to position a selected dispenser, containing discs impregnated with a particular antibiotic, above or adjacent to a specific area of the petri dish, and a disc is dispensed. The moveable platform can then be repositioned to bring a dispenser containing a second type of antibiotic disc into position relative to the petri dish. A disc of this second antibiotic can then be dispensed into the petri dish. The petri dish can be repositioned prior to the dispensing such that subsequent discs are dispensed at a pre-determined distance from each other, allowing for a clear area for the antimicrobial interaction with different microorganisms to take place and be observed without interference from adjacent colonies of microorganisms. The system can continue to dispense discs at a number of pre-determined positions within the petri dish.

In order to maximize the flexibility of such a system, it is desirable to have a wide variety of antibiotic discs available for dispense onto the plate. To ensure against cross-contamination between the varying antibiotics being dispensed by the system, it is unacceptable to place multiple antibiotics within the same dispenser. Thus, a separate dispenser is required to be mounted upon the moveable platform for each individual type of antibiotic that will be dispensed. Consequently, prior art systems have been limited by the mechanical constraints on the number of dispensers that can be reasonably mounted upon a moveable platform that can be accurately and selectively positioned over the culture plate or culture plate support that delivers the culture plate into alignment with a dispenser to receive a microbial disc dispensed by such dispenser. Various arrangements have been proposed, including the mounting of dispensers about the circumference of a carousel that can be rotated about a central hub so that a particular dispenser is positioned over a container located on the periphery of the carousel. See, for example, U.S. Pat. No. 8,996,163, Disc Dispensing Device, Tubular Container for Use in such a Disc Dispensing Device and Method of Dispensing Discs, and U.S. Pat. No. 9,557,343, Disc Dispensing Device, Tubular Container for Use in such a Disc Dispensing Device and Method of Dispensing Discs, both of which are assigned to BD Kiestra B.V and are incorporated by reference herein. However, as the number of dispensers is increased, such single carousel-based systems can become quite large as the diameter of the carousel is increased to accommodate more and more dispensers. Testing equipment having a large physical footprint is generally undesirable in the controlled and typically space-limited environment of a commercial sample testing laboratory. In addition, as a consequence of employing a large diameter dispenser-laden carousel, the mean time required to rotate the carousel to dispense a specific antibiotic will be greater than that for a smaller diameter carousel, assuming the angular velocity at which the carousels can be rotated is held to the same limit. This will result in decreased system throughput. Also, as the carousel size increases, so likely would its mass, requiring more powerful driving mechanisms and resulting in higher system costs. In a single carousel the achievable cartridge dispenser density is therefore limited. In addition, large carousels are more cumbersome to handle, store and clean.

Therefore, there is a need to provide an improved testing system and method for dispensing a wide variety of reagents, from separate, dedicated dispensers, wherein a selected dispenser is quickly and accurately positioned to dispense a selected reagent onto a testing medium within a small footprint. This functionality needs to be achieved without adversely impacting the throughput rate at which reagents are dispensed.

BRIEF SUMMARY OF THE INVENTION

The present invention provides an improved system and method for the selection and dispensing of reagents onto a target testing medium in an automated laboratory environment. The invention utilizes multiple carousels rotatably-mounted upon a central turntable. The position of the central turntable, as well as the rotation of each carousel is controlled by a microprocessor-based control system. Multiple dispensers, each capable of storing and dispensing a particular reagent, are mounted about the circumference of each carousel. The testing medium is positioned at one or more loading stations. The control system directs the central turntable to a position from which a selected one of the carousels can be rotated so as to position a selected dispenser above the testing medium. The selected dispenser is then actuated to release a predetermined amount of reagent onto the testing medium, in the antimicrobial case an impregnated disc. The invention can be implemented so that multiple reagents can be simultaneously dispensed, each from an associated dispenser, onto a culture plate with single or multiple culture mediums. One example of a suitable testing medium is a culture medium. Plated culture media are well known to those skilled in the art and are not described in detail herein. Culture medium and testing medium are used interchangeably herein. Each of these simultaneously actuated dispensers are positioned over the targeted culture medium(s) positioned at one or more loading stations.

One embodiment of the reagent dispensing system has a control system comprising a processor and a memory. The system has a rotatably mounted central turntable positionable in response to commands received from the control system. The system also has a plurality of carousels, rotatably mounted upon the rotatably mounted central turntable, each positionable in response to command received from the control system. The system further includes a plurality of dispenser cartridges, mounted about a circumference of the plurality of carousels. Mechanical actuation of a dispenser cartridge results in dispensing of a predetermined reagent contained within the actuated dispenser cartridge. Optionally, the mechanical actuator is adapted to actuate at least one of the plurality of dispenser cartridges from a command received from the control system.

One example of the predetermined reagent is a disc. Optionally the disc is dispensed from the cartridge using a vertical plunger. Optionally, the vertical plunger is actuated by a rotating cam, wherein the rotating cam is responsive to a command received from the control system.

Optionally the reagent dispensing system further includes a plunger assembly housing the vertical plunger. The plunger assembly can be brought into proximity with a medium upon which the disc is to be dispensed prior to actuating the vertical plunger.

In operation, the predetermined reagent is dispensed onto a surface of a testing medium. The testing medium is typically a culture medium disposed in a culture plate. The reagent dispensing system optionally has a proximity sensor, in communication with the control system and adapted to scan and measure the surface of the testing medium. One example of a proximity sensor is an ultrasonic sensor.

In operation a disc reservoir is placed in the dispenser cartridge. The disc reservoir has a machine-readable identification label affixed to it. The system has at least one optical sensor in communication with the control system and adapted to read the machine-readable identification labels, wherein the memory of the control system contains information associating each machine-readable label with at least one of: (a) a type of reagent contained within the dispenser cartridge (and the disc reservoir held therein), or (b) an amount of reagent available within the machine-readable labeled dispenser cartridge for dispensing. The machine-readable identification label typically has a barcode, and the at least one optical sensor is a barcode reader.

The culture plate optionally has a machine-readable identification label affixed to it. The system further includes at least one optical sensor in communication with the control system and adapted to read the machine-readable identification label. The memory of the control system contains information associating the machine-readable identification label with at least one of: (a) a type of testing medium contained in the plate, (b) a type of reagent that has been dispensed onto the testing media, (c) a location upon the testing medium at which reagents have been dispensed, (d) the type of any additional reagents dispensed onto the testing medium, or (e) the location upon the testing medium that is available for dispensing additional reagents thereon. Again, the machine-readable identification label typically carries a barcode, and the at least one optical sensor is a barcode reader.

Optionally, at least two of the carousels are mounted concentrically.

Also described herein is a method for automated dispensing of reagents in a system. The system includes a control system comprising a processor and a memory. The system also includes a rotatably mounted central turntable positionable in response to commands received from the control system. The system also includes a plurality of carousels, rotatably mounted upon the rotatably mounted central turntable, each independently positionable in response to commands received from the control system. The system further includes a plurality of dispenser cartridges, mounted about a circumference of each of the plurality of carousels. Mechanical actuation of a dispenser cartridge results in dispensing a predetermined measure of a reagent contained within the actuated dispenser cartridge. The system also includes at least one test medium (e.g. a culture medium) carried by a culture plate.

According to the method describe herein the rotatably mounted central turntable is positioned so as to place a selected carousel in a position proximate to the at least one test medium. The selected carousel is rotated to position a selected dispenser cartridge in a position to dispense a predetermined measure of reagent on to the at least one test medium. The selected dispenser cartridge is actuated to dispense the predetermined measure of reagent on to the test medium.

Optionally the predetermined measure of reagent is a disc. The discs are provided to the dispenser cartridge as a disc reservoir. Actuating the selected dispenser cartridge causes the disc to be dispensed via a vertical plunger. Optionally a cam actuates the selected dispenser cartridge. As noted above, one example of a testing medium is a culture medium carried by a culture plate. Optionally, a surface of the testing medium is assessed with a proximity sensor for deposit of the disc on the surface.

Optionally, each dispenser cartridge has a machine-readable identification label associated with it. Optionally, the machine-readable identification label is carried by the disc dispenser held in the dispenser cartridge. The machine-readable identification label is read with an optical sensor. Data associated with the read machine-readable identification label is accessed from the memory of the control system. The accessed data is indicative of at least one of: (a) a type of reagent contained within the dispenser cartridge having the machine-readable identification label affixed thereto, or (b) an amount of reagent available within the dispenser cartridge having the machine-readable identification label affixed thereto.

Optionally, the culture plate has a machine-readable identification label affixed to it. According to the method the machine-readable identification label is read with an optical sensor. Data associated with the read label is accessed from the memory of the control system. The accessed data is indicative of at least one of: (a) a type of test medium or culture medium contained in the culture plate, (b) a type of reagent that has been dispensed onto the test medium, (c) a location upon the test medium at which reagents have been dispensed, (d) optionally, the type of additional reagents to be dispensed onto the test medium, or (e) optionally, the location upon the test medium that is available for the dispensing of additional reagents.

BRIEF DESCRIPTION OF THE DRAWINGS

The features, aspects, and advantages of the present invention will become better understood with regard to the following description, appended claims, and accompanying drawings in which:

FIG. 1 is perspective view of a four-carousel cartridge-based dispensing system according to one embodiment of the present invention.

DETAILED DESCRIPTION

Figure 2A:
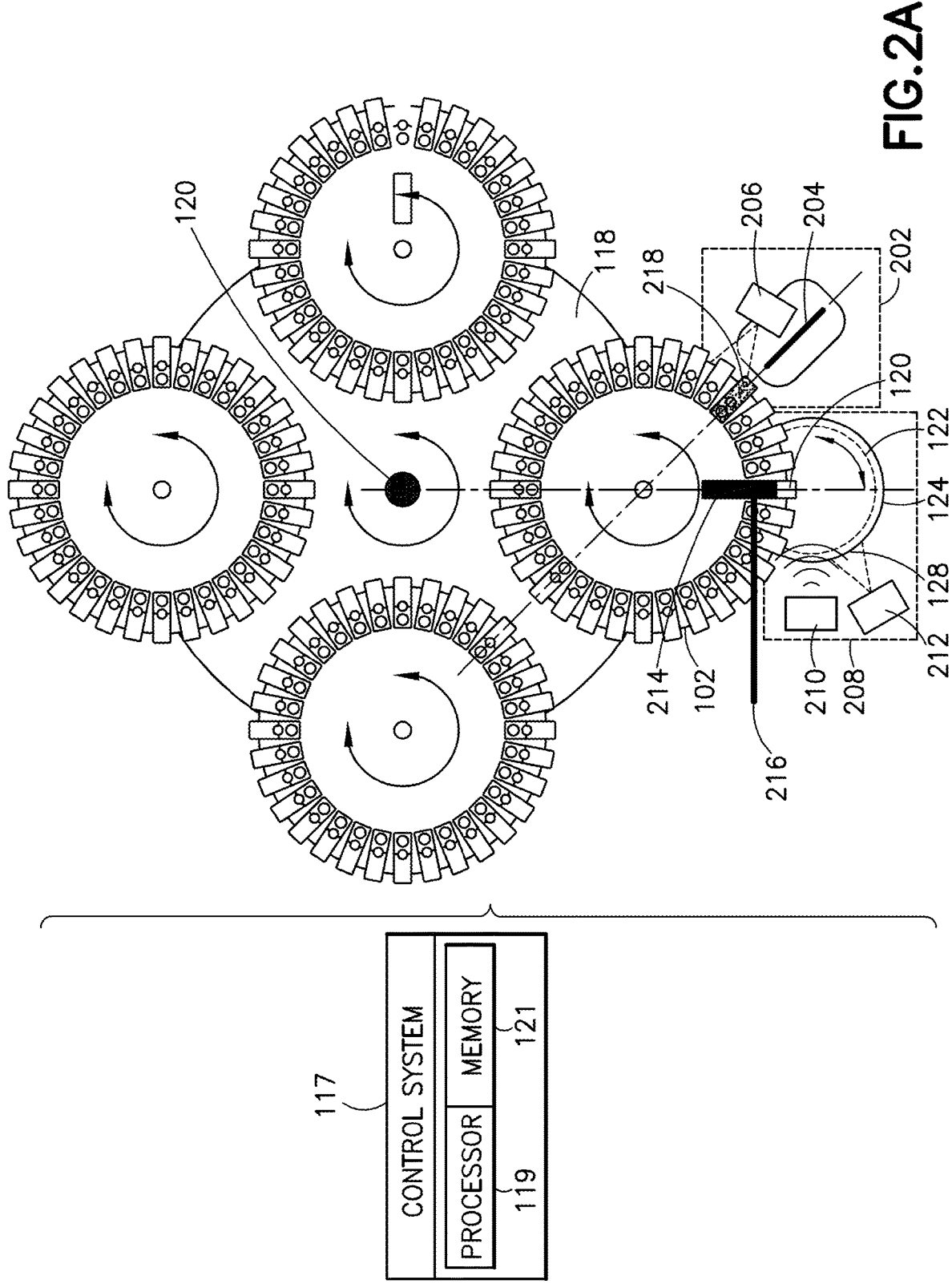
FIG. 2A is a top view of the four-carousel cartridge-based dispensing system of FIG. 1 positioned to prime a dispenser.

The term "turntable" as used herein is used to describe the rotatable support for carousels 102, 104, 106, etc. The term, as used is not meant to require that the turntable is circular. In fact, as described herein, the geometry of the turntable is largely a matter of design choices. The turntable is used to convey the carousels into the necessary positions so that the carousel can deliver the selected reagent disc dispensing cartridge into alignment with the culture plate so that the selected reagent disc dispensing cartridge may dispense a disc onto the selected location of the culture plate.

FIG. 1 shows a partial, perspective view of a four-carousel embodiment of the invention. As shown, carousels 102, 104, 106 and 108 are rotatably mounted upon central turntable 110. Each of these carousels is configured to be rotated in a clockwise or counter-clockwise direction about center hubs 111, 112, 114 and 116, respectively. This rotation is responsive to control signals received from a microprocessor-based control system (117). This rotation of each carousel may be driven by any conventional mechanism well known to those skilled in the art. One example is a servo or stepper motor mounted upon the central turntable through a system of belts, gears or other similar transmission arrangements known in the art and which can be driven by such motors. Such mechanisms are well known in the art and not described in detail herein. Similarly, the central turntable 118 is configured to be rotated clockwise or counter-clockwise about center hub 120 by a direct-drive or transmission-linked electric motor system, responsive to control signals from the microprocessor-based control system. Rotatable plate put a center hub by a direct-drive or transmission-linked electric motor system, responsive to control signals from the micro-processor-based control system. Such a microprocessor system would include a processor 119, memory 121, various sensors (optical, ultrasonic, etc.), motor controllers, and a user interface.

Figure 2B:
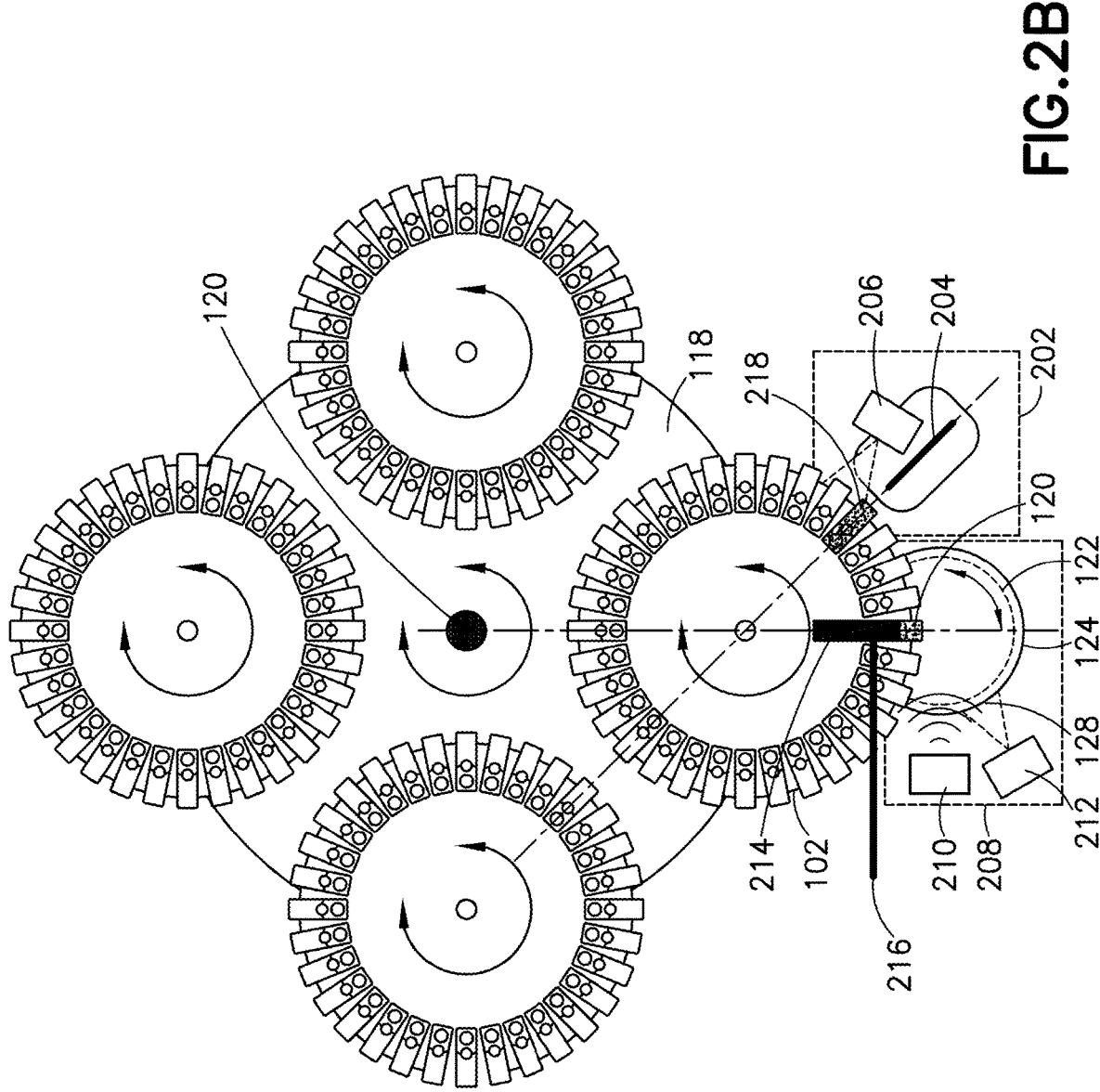
FIG. 2B is a top view of the four-carousel cartridge-based dispensing system of FIG. 1 positioned to dispense a reagent disc.

Each carousel in this embodiment has thirty-two radially-mounted, removeable reagent dispensers. In FIG. 1, for reasons of visual clarity, a limited number of dispenser groupings (130, 132, 134 and 138) are illustrated on each of the four carousels (102, 104, 106 and 108, respectively). FIG. 2 provides a top-view of the cartridge-based dispenser of FIG. 1, showing 30 cartridge dispensers 218 mounted on each of the carousels, bringing the total number of dispensers in the system to 128. Disc primer station 202 (consisting of actuator 204 and barcode reader 206), loading station 208 (consisting of plate platform 122, ultrasonic proximity sensor 210, barcode reader 212), composite cam 214 and cam shaft 216 are also illustrated in FIGS. 2A and 2B.

Figure 3A:
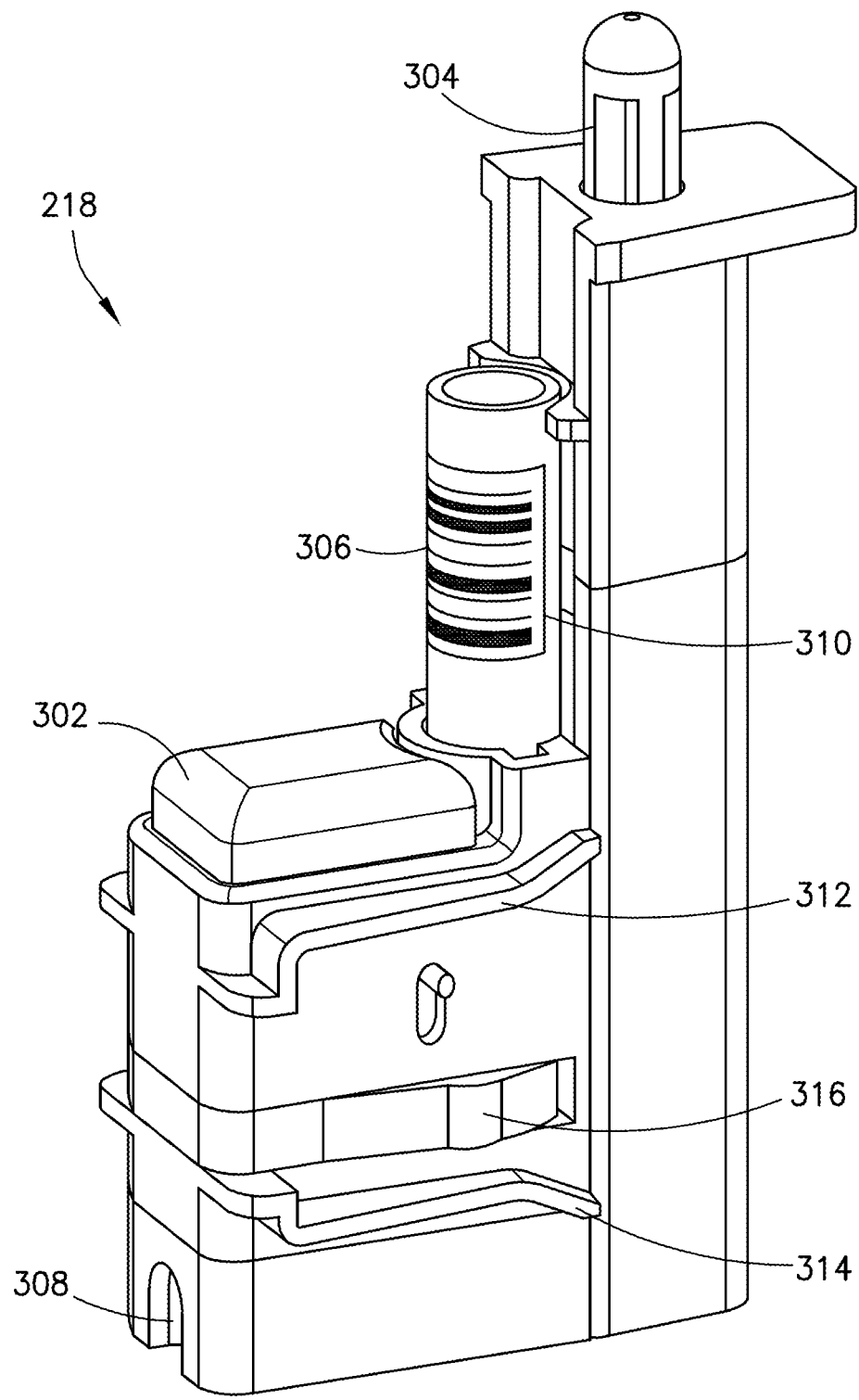
FIG. 3A is the perspective view of a reagent disc dispensing cartridge utilized in the multiple carousel cartridge-based dispensing system of FIG. 1.

A perspective view of exemplary cartridge dispenser 218 is shown in FIG. 3A. The cartridge dispenser includes outer casing 302, plunger assembly 303, vertical plunger 304, reagent disc reservoir 306, reagent disc priming port 308, and machine-readable identification label 310. As shown, the outer casing of dispenser 218 includes insertion guides 312 and 313. The guides 312 and 313 mate with a complementary arrangement at each of the dispenser mounting locations upon a given carousel. This permits dispensers to be securely affixed to a carousel, while facilitating easy removal when needed. This click-in, click-out arrangement permits a depleted dispenser to be quickly replaced with a full dispenser, or for a dispenser containing a particular reagent to be replaced with one containing a different reagent. Similar mountings are well known in the art and can be fashioned from nylon or other polymers.

Figure 3B:
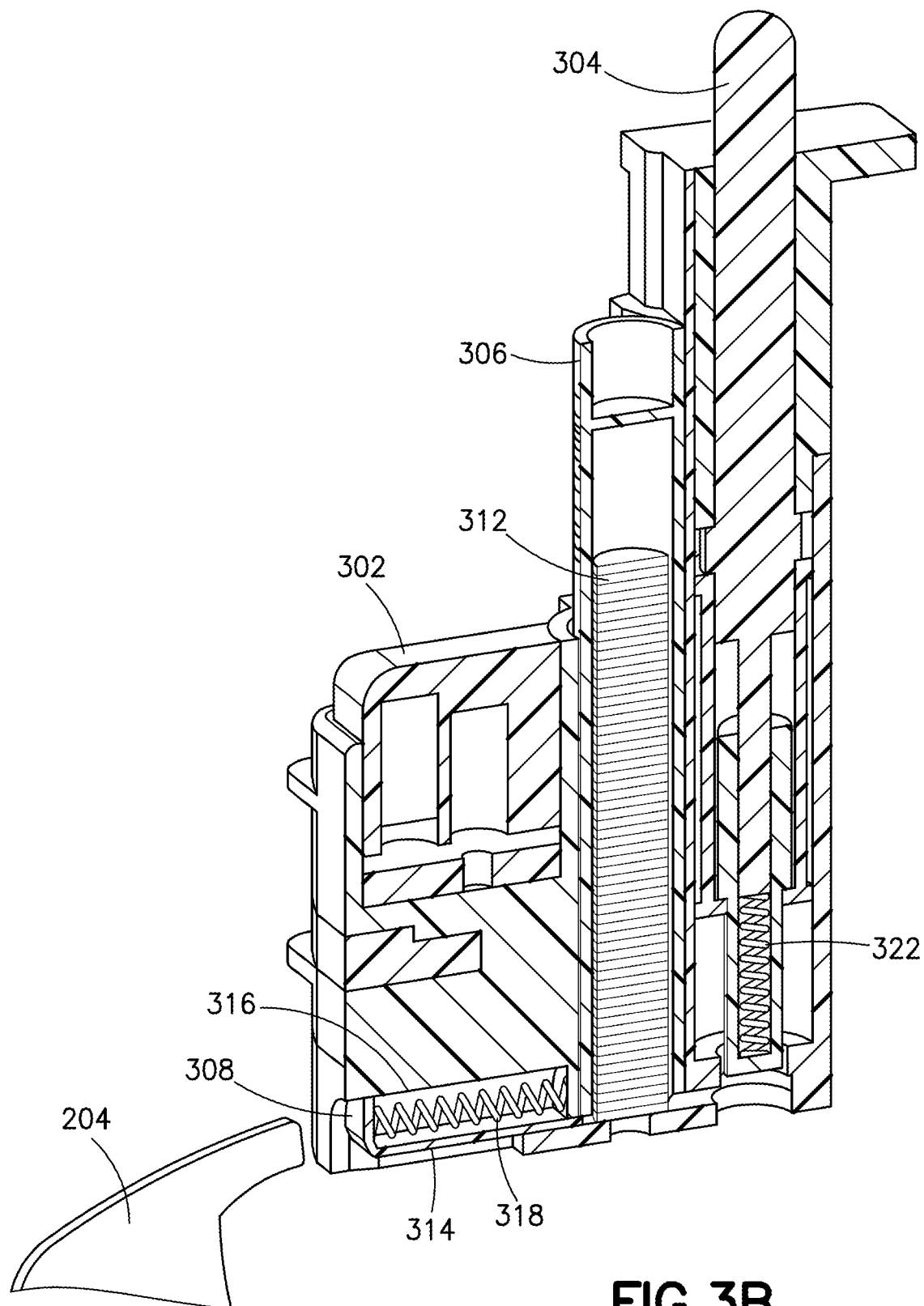
FIG. 3B provides a side, front and cutaway view of a composite cam.

FIG. 3B provides a side, front and cutaway view of composite cam 214 and cam shaft 216. As shown, the composite cam consists of outer cams 318 and 320, inner cam 322. The gap (g) between the inner surfaces of the outer cams is fixed to a distance that is greater than the diameter of vertical plunger 304, thereby permitting the outer cams to be rotated without contacting the vertical plunger.

Figure 3C:
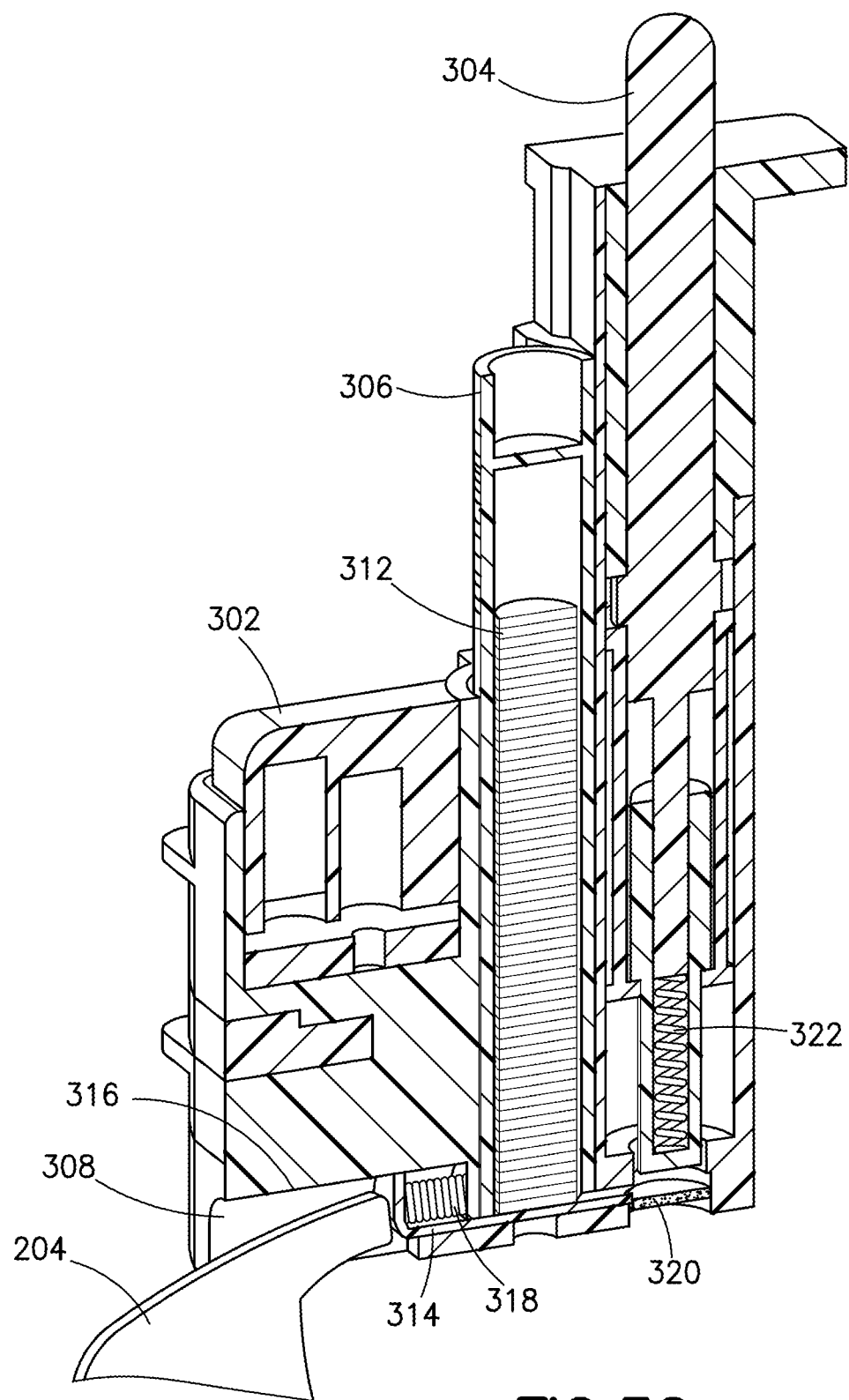
FIG. 3C is partial cut-away perspective view of the reagent disc dispensing cartridge of FIG. 3A in an unprimed state.

A cross-sectional view of the dispenser is provided in FIG. 3C. Reagent discs 312 are shown to be stacked within reagent disc reservoir 306. Typically, all of the reagent discs loaded in a particular dispenser contain identical reagent(s). The control system's memory contains information associating the unique machine-readable label (310) affixed to a given reservoir with the particular type of reagent discs contained therein. The control system memory can also store information associating a particular dispenser with a particular slot upon a particular carousel (one of four in this particular embodiment). This information can be used by the control system to selectively position the central turntable and the carousels so as to situate a selected dispenser at a particular location within the dispensing system to dispense a selected type of reagent disc on a selected location of the culture plate. In addition, when a carousel is replaced a configuration sequence will read all of the standard or rotationally insensitive circumferential barcodes, which enable reading irrespective of the label position on the installed disc reservoirs to construct the positional map. Disc primer 314 is shown to be mounted within outer casing 302 in manner that permits horizontal movement within cavity 316, and biased toward priming port 308 by spring 324. Disc primer actuator 204 is also illustrated in FIG. 3C.

The operation of dispensing a reagent disc containing a particular reagent from the cartridge-based dispensing system requires the coordinated operation of central turntable 110, carousels 102, 104, 106 and 108, plate platform 122, and reagent disc primer actuator 204. The positioning and actuation of these components is controlled by the microprocessor-based control system. The process operation begins with the placement of a medium (126) containing culture plate 124 upon plate platform 122. This placement can be accomplished by an automated plate handling system, well-known in the art, or it can be performed manually. After placement of the culture plate, plate platform 122 is rotated by the microprocessor control system so that machine-readable label 128 is positioned for reading by barcode reader 212. The read barcode can be cross-referenced with information stored in the memory of the microprocessor-based control system, so as to check/confirm that culture plate 124 is a proper plate for deposition of the reagent from dispenser 218. The label 128 is also used to orientate the plate rotationally and to place the reagent discs relative to the label position.

As a consequence of a pre-programmed routine, or in response to instructions received through a user interface, the control system actuates central turntable 118 and the relevant carousel 102, 104, 106 or 108 so as to bring a dispenser (218) containing the desired reagent discs into alignment with disc primer actuator 204. Disc primer actuator 204 is mounted relative to the plane of the carousels so as to permit the disc primer actuator, when activated, to enter dispenser priming port 308 of properly aligned dispenser 218.

Once dispenser 218 is aligned with disc primer actuator 204, machine-readable label 310 is read by barcode reader 206. The barcode information is cross-referenced with the control system's memory to confirm that it is associated with the type of reagent disc that the system was instructed to dispense. If the proper association is confirmed, the dispensing process continues. If there is a mismatch, the system will generate an error signal indicating that the desired dispenser has not been properly positioned in alignment with the disc primer. This could be the result of various system failures, including the malfunctioning of the central turntable or individual carousel positioning systems. The error signal would serve to alert a technician or operator to rectify the situation. Assuming that the proper barcode/reagent association is confirmed, the control system would send a command activating disc primer actuator 204.

Figure 3D:
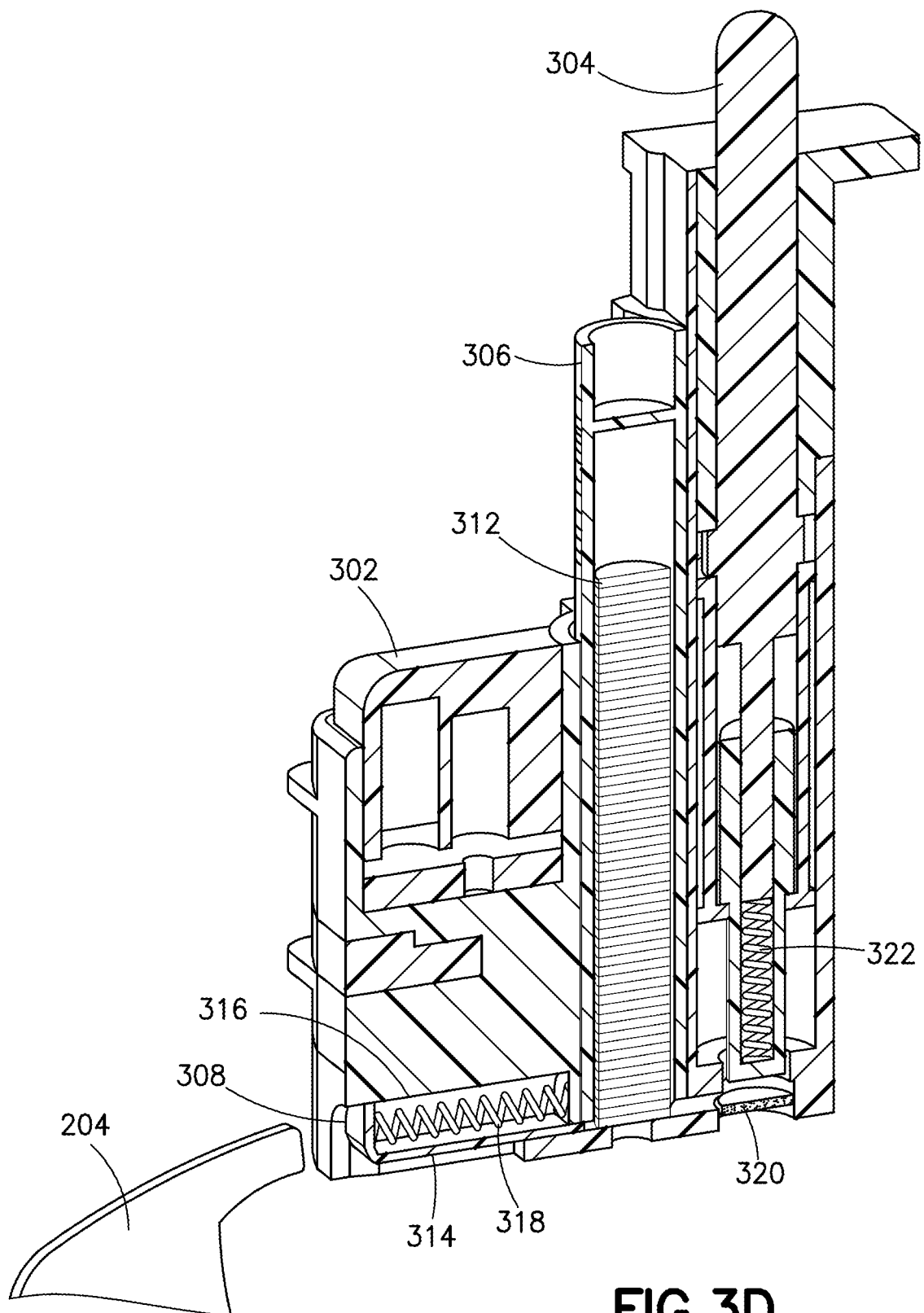
FIG. 3D is partial cut-away perspective view of the reagent disc dispensing cartridge of FIG. 3A in the process of being primed.
Figure 3E:
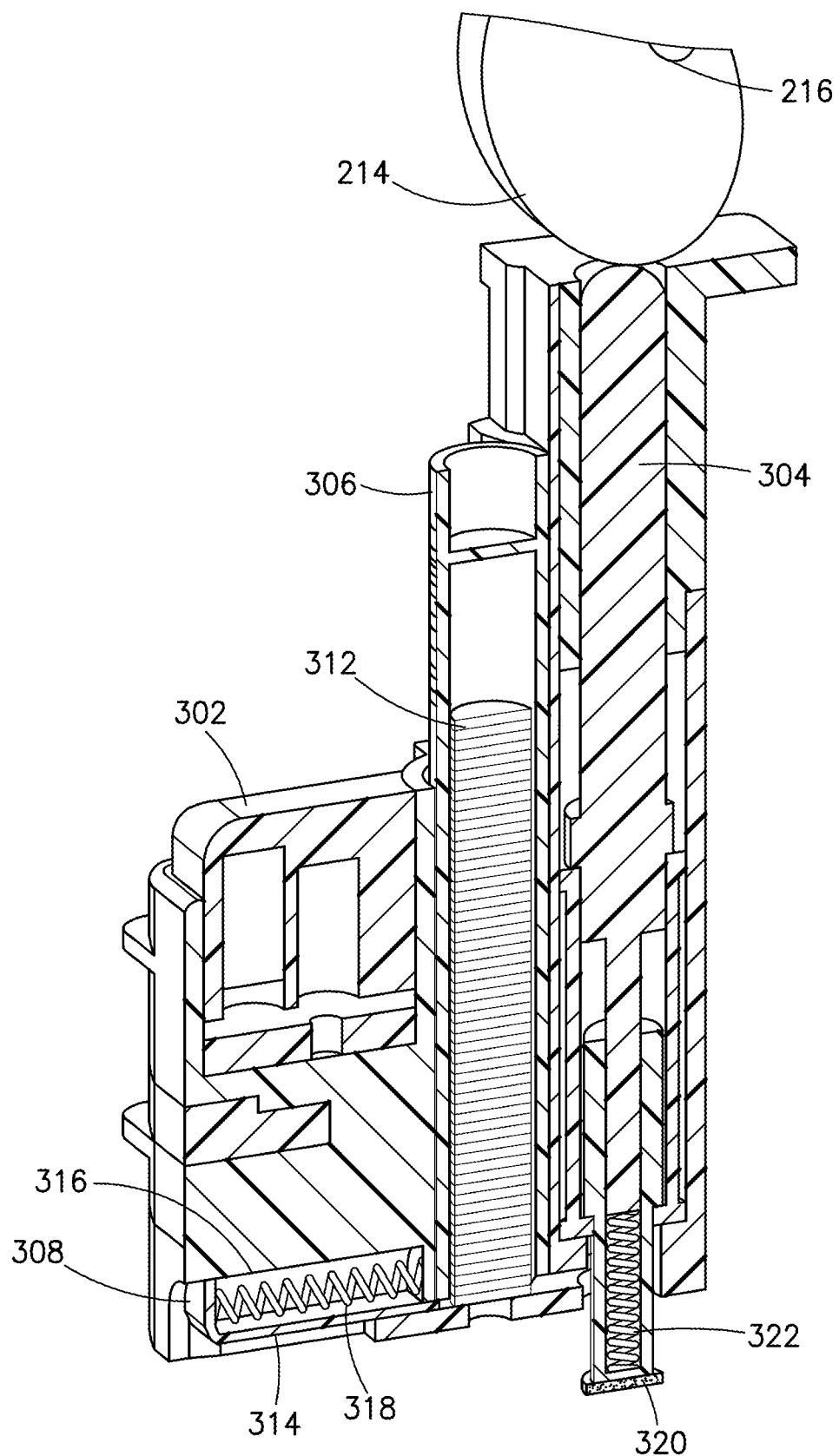
FIG. 3E is partial cut-away perspective view of the reagent disc dispensing cartridge of FIG. 3A in a primed state.
Figure 3F:
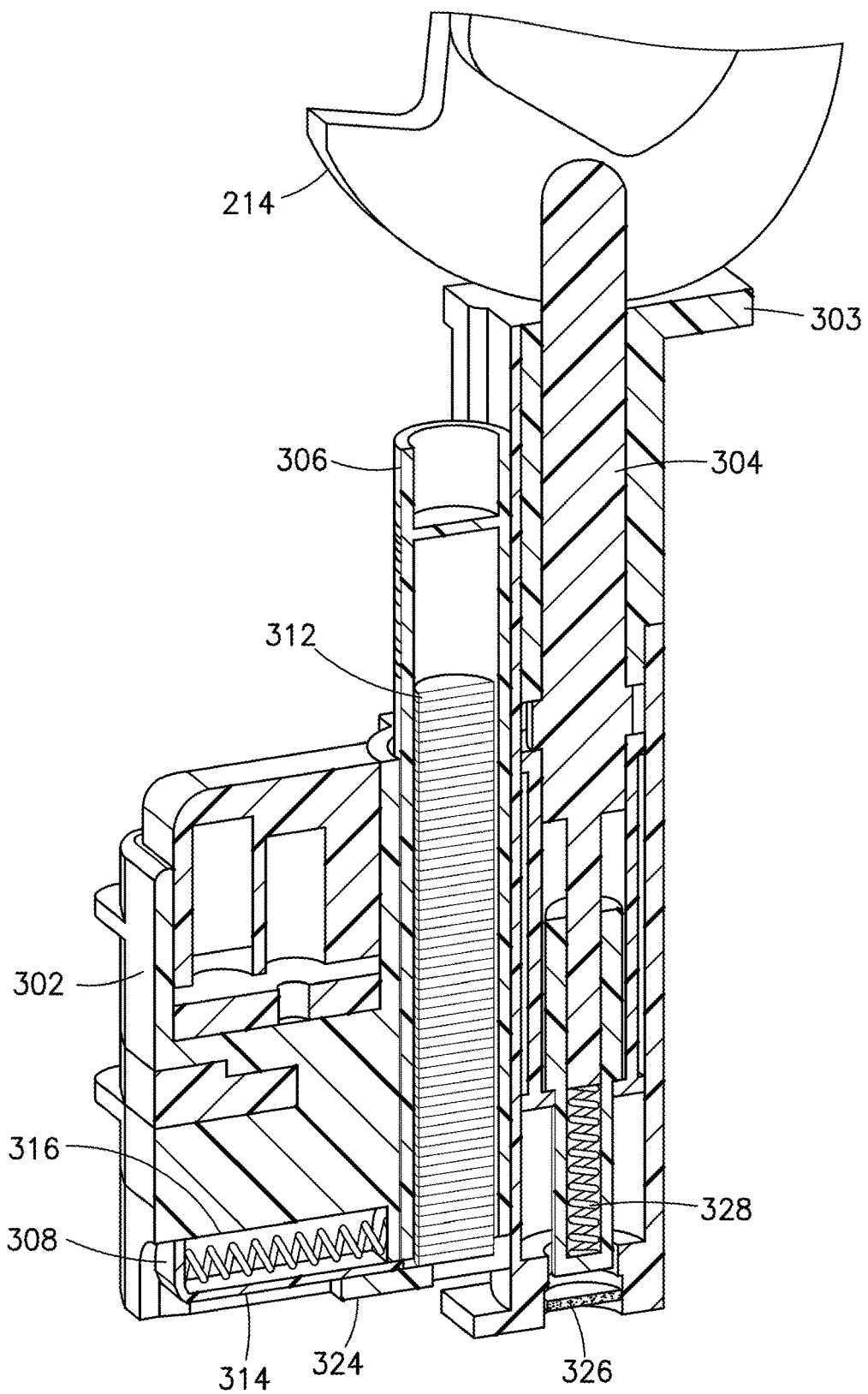
FIG. 3F is partial cut-away perspective view of the reagent disc dispensing cartridge of FIG. 3A engaged by an outer cam.
Figure 3G:
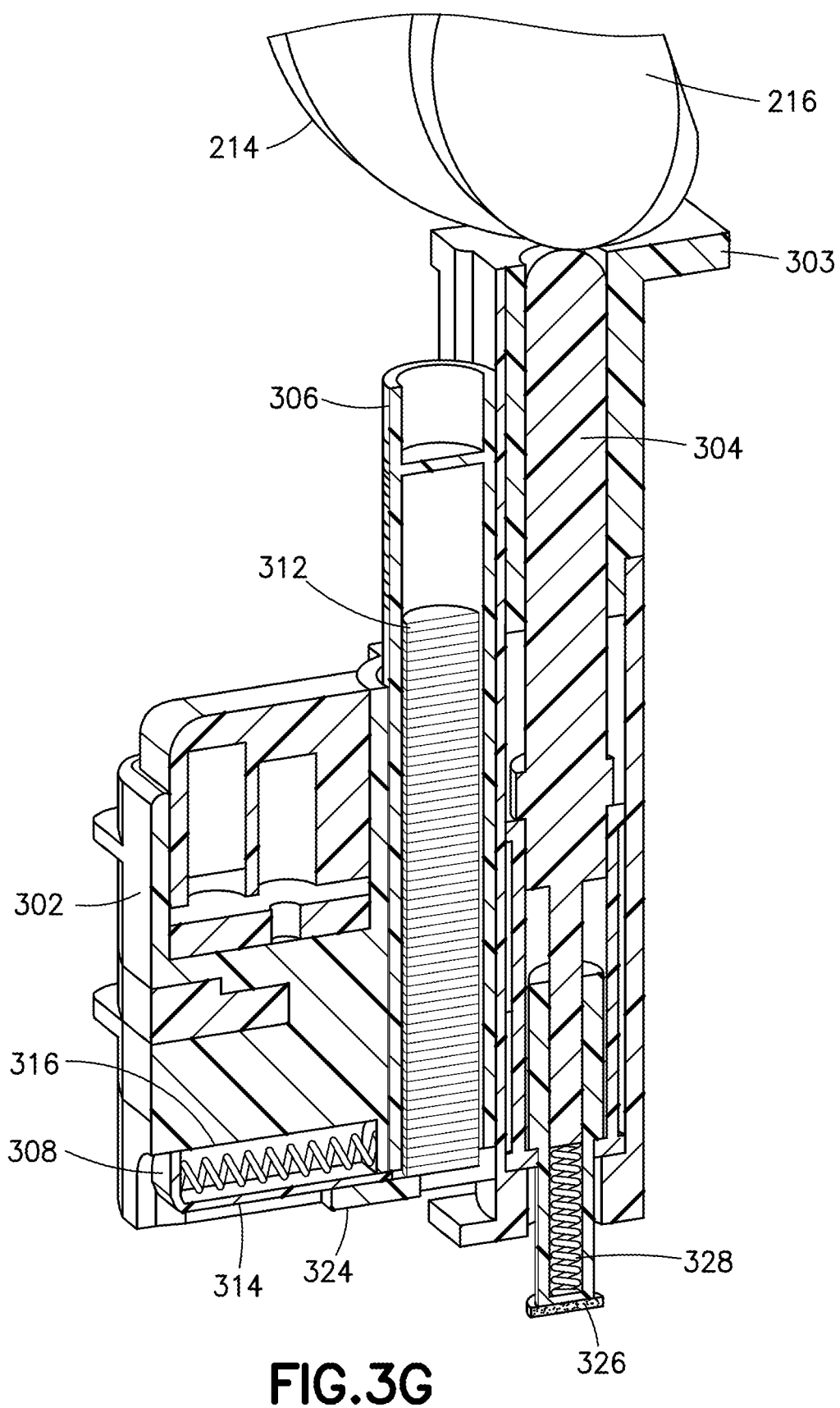
FIG. 3G is partial cut-away perspective view of the reagent disc dispensing cartridge of FIG. 3A fully engaged by a composite cam.

This activation causes reagent disc primer actuator 204 to be urged toward and into dispenser priming port 308 (see FIG. 3D). This activation can be electro-mechanical, hydraulic, pneumatic, etc. As disc primer actuator 204 enters dispenser priming port 308 it urges reagent disc primer 314 toward reagent disc reservoir 306, causing it to translate through cavity 316, compress spring 324, and push bottommost reagent disc 326 out from under the stack of reagent discs (312) and into position directly under vertical plunger 304. As shown in FIG. 3E, disc primer actuator 204 then retracts, spring 324 urges disc primer 308 back to its initial position, and reagent disc 326 remains positioned under vertical plunger 304. The disc primer actuator 204 is monitored to confirm it has travelled the full distance and dispensed a reagent disc. If the reagent disc primer actuator 204 fails to actuate or is otherwise prevented from advancing a disc from the disc reservoir 306, indicating that that the disc reservoir is empty or jammed, and an error state is raised and a technician summoned. The vertical plunger 304 remains biased by internal springs (not shown) in an upward, extended position throughout this process. The control system then sends commands that reposition a carousel (e.g. 102) so that dispenser 218 is positioned over culture plate 124, and so that the top of plunger assembly 303 and vertical plunger 304 are positioned directly below composite cam 214.

After dispenser 218 is positioned as described above, the control system signals a drive system (not pictured) linked to cam shaft 216 (FIG. 4A) to rotate the cam shaft 360° in a clockwise direction. This rotation causes composite cam 214, which is fixed to cam shaft 216, to rotate about the axis of the shaft, causing composite cam 214 to contact, and ultimately fully depress, vertical plunger 304. This action is illustrated in FIGS. 3F-G and 4A-D.

Figure 4A:
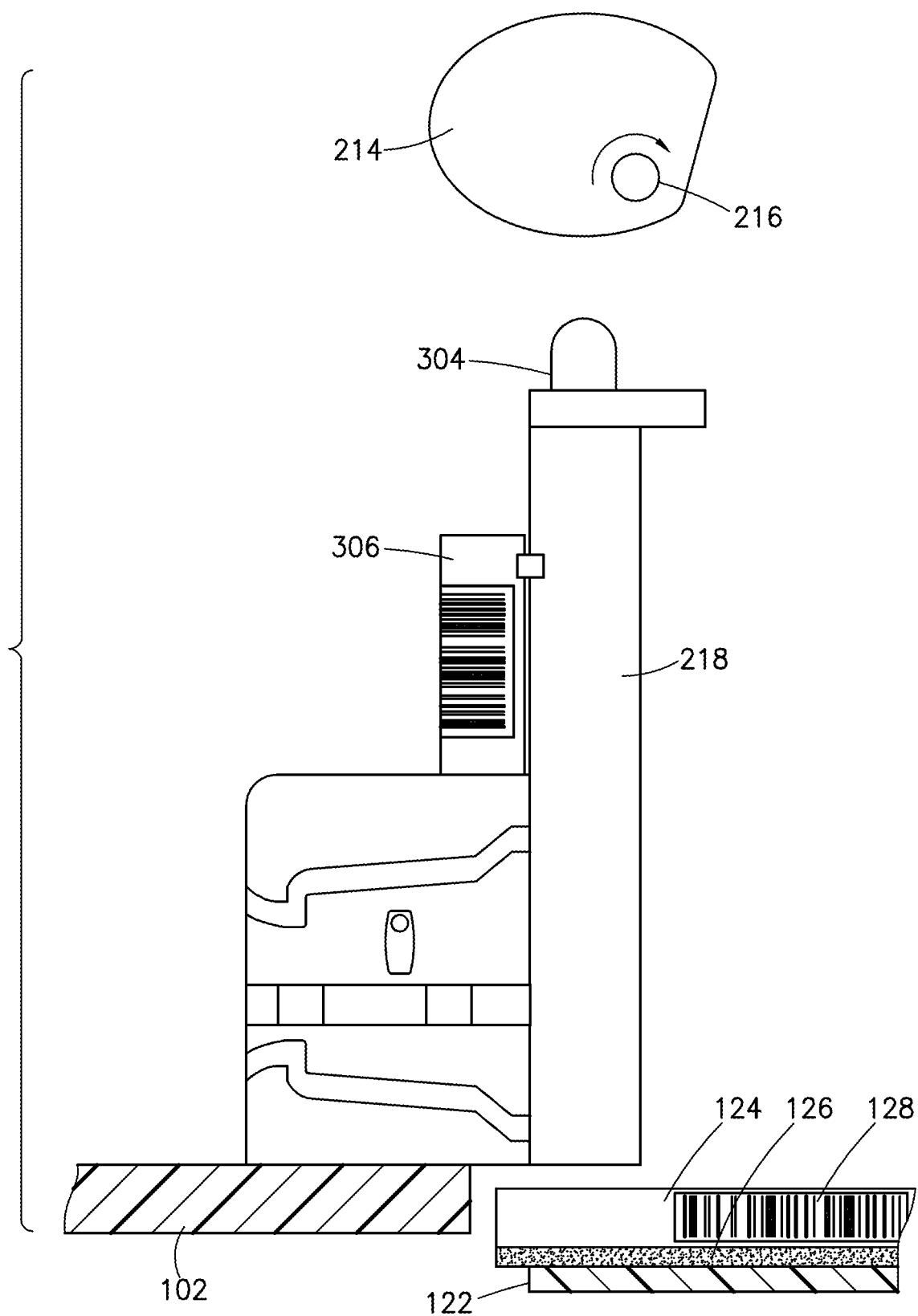
FIG. 4A is a side view of the reagent disc dispensing cartridge of FIG. 3A, prior to engagement with the composite cam.
Figure 4B:
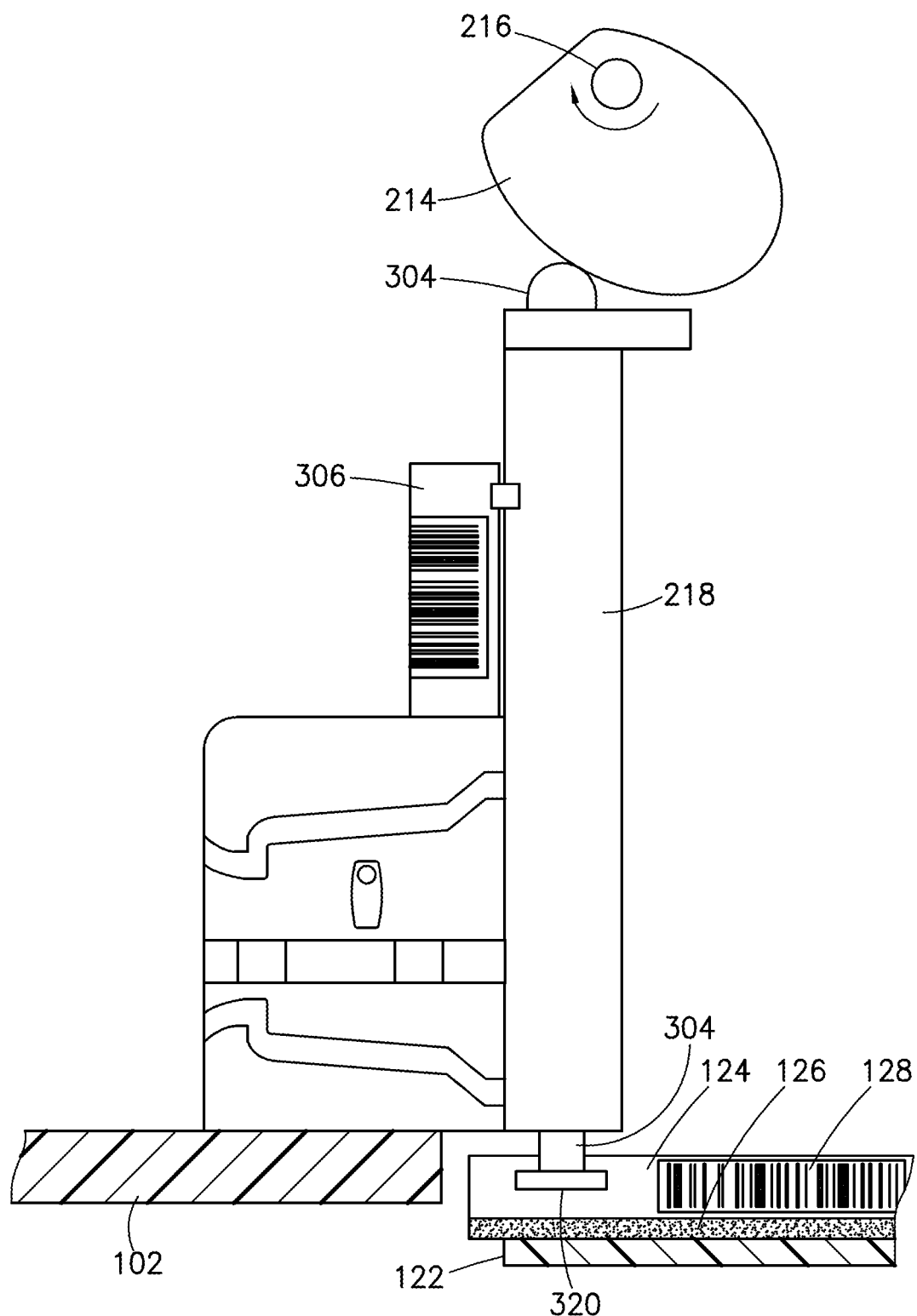
FIG. 4B is a side view of the reagent disc dispensing cartridge of FIG. 3A, partially engaged by an outer cam.
Figure 4C:
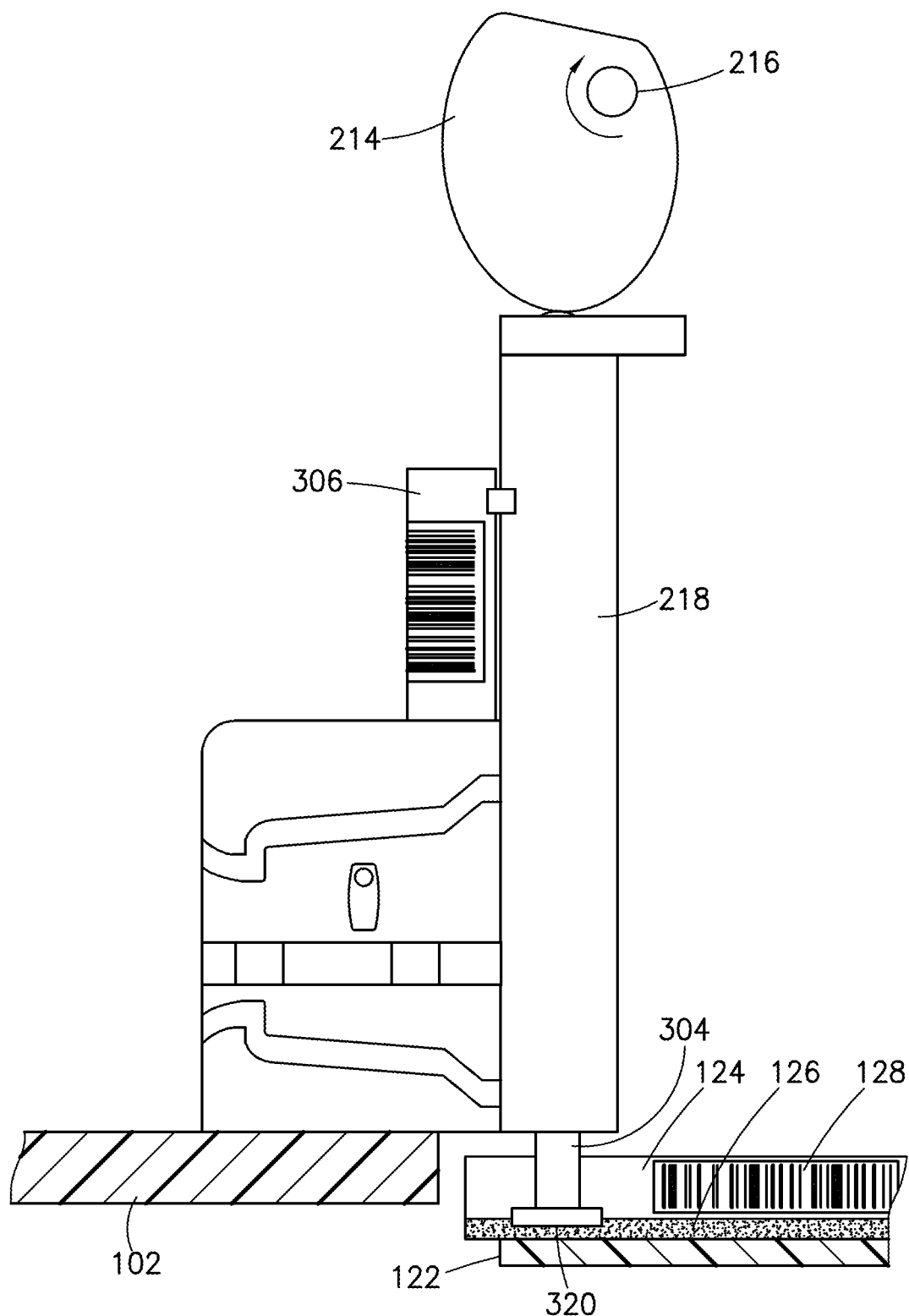
FIG. 4C is a side view of the reagent disc dispensing cartridge of FIG. 3A, fully engaged by a composite cam.
Figure 4D:
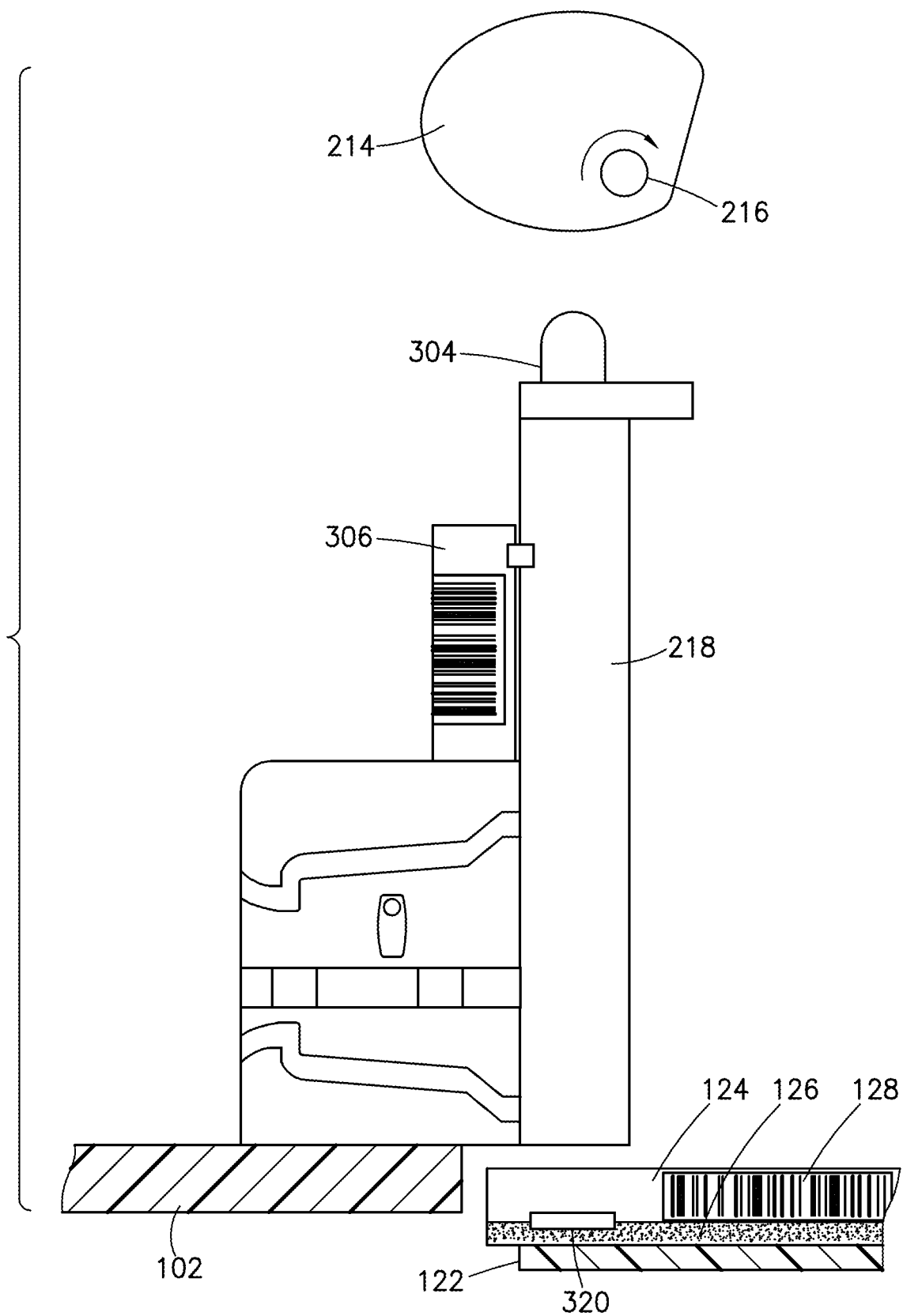
FIG. 4D is a side view of the reagent disc dispensing cartridge of FIG. 3A, following engagement with a composite cam.

FIG. 4A shows a side-view of dispenser 218 prior to engagement with composite cam 214. The top portion of vertical plunger 304 is biased upwards by internal springs (not shown) in an extended position (see also, FIGS. 3C and 3E). As shown in FIG. 4A, neither of the outer cams (outer cam 320 is shown), nor the inner cam (the position of which is depicted by the dotted-lined shaded area) are in contact with dispenser 218. The position of cam shaft 216 is represented by the dotted line circular area. In FIG. 4B composite cam 214 has been rotated clockwise so that outer cams 318 and 320 (only 320 is shown) come into contact with and depress the top of plunger assembly 303, causing the compression of internal springs (not shown) and advancing plunger assembly 303 downward toward the surface of culture medium 126. Note that the outer cams do not engage vertical plunger 304. Rather the spacing, g, between the inner walls of the outer cams permits then to engage plunger assembly 303 without ever contacting vertical plunger 304. In FIG. 4C composite cam 214 is shown rotated to a position where inner cam 322 fully engages with vertical plunger 304. In this fully depressed state, the bottom of vertical plunger 304 pushes reagent disc 326 with a predetermined force, provided by the tamper spring 328 onto the surface of culture medium 126 in culture plate 124 (see also, FIG. 3F). Composite cam 214 then rotates a full 360° back to its initial starting position as shown in FIG. 4D. Plunger assembly 303 and vertical plunger 304 (biased by internal springs which are not shown) retract upward, away from plate 124.

The two-stage dispensing action described above offers advantages over systems employing a vertical plunger and a static plunger assembly. During the first dispensing stage, plunger assembly 303 is engaged by the outer cams 318 and 322 and lowered toward the surface of the medium. The inner cam (322) then engages vertical plunger 304, causing the opposite end of that plunger to extend below plunger assembly 303 and push a reagent disc onto the surface of the target medium. By first lowering the plunger assembly so as to bring it into closer proximity with the surface of the target medium, the distance that the vertical plunger must traverse in pushing a reagent disc on to the surface of the medium is minimized. The combination of the mechanical stability afforded by the plunger assembly being brought into close proximity with the medium surface and the consequential reduction the distance the vertical plunger must extended to dispense a disc results in increased disc placement accuracy and repeatability.

The self-contained nature of each dispenser offers numerous advantages for a dispensing system. As was previously discussed, each of the dispensers can be readily connected/ disconnected from a given carousel. There are no associated power connections or complex mechanical linkages. The cam actuation permits each dispenser to be unencumbered by any such connection making them readily interchangeable with one another and avoiding any physical linkage with the actuation mechanism that might impede the rotation of a carousel. This self-contained nature also provides an inherent guard against cross-contamination. The mechanics that come into contact with and ultimately facilitate the ejection of a reagent disc are fully contained within a dispenser. There is no dispensing mechanism associated with a loading station that would come into contact with discs from multiple dispensers.

With the dispensing of reagent disc 326, the memory of the control system is updated so that the count of the number of reagent discs stored in reagent disc dispenser 306 of reagent disc dispensing cartridge 218 is reduced by one. The memory of control system maintains a similar disc count for each of the dispensers mounted upon the four carousels, enabling the dispensing system to maintain an accurate inventory of the number of discs within every reagent disc dispensing cartridge within the system. The system can then avoid selecting an empty dispenser and provide alerts to an operator (via a user interface) when particular dispensers are becoming depleted.

Once a reagent disc is dispensed onto the culture medium contained within a given culture plate, that culture plate may be removed from the dispensing system if no additional reagent discs are to be deposited thereon. If additional reagent discs are required to be dispensed on the culture plate, commands from the microprocessor-based control system cause the culture plate to be rotated by platform 122 to properly align a different region of the medium within the plate so that an additional reagent disc can be deposited thereon. This additional disc can be dispensed from any of the reagent disc dispensing cartridge mounted upon any one of the four carousels. In a particular embodiment of the invention, a minimal radial spacing of 60° between deposited reagent discs is imposed. This permits six reagent discs to be equidistantly positioned on a single plate, maximizing the utility of any given plate without placing the reagent discs in too close of a proximity of one another, and thereby risk cross-contamination or false results due to overlapping areas into which antibiotic from adjacent discs has diffused and the effects of multiple antibiotics (or antibiotic concentrations) on the microorganism colonies in that overlapping region.

Figure 5:
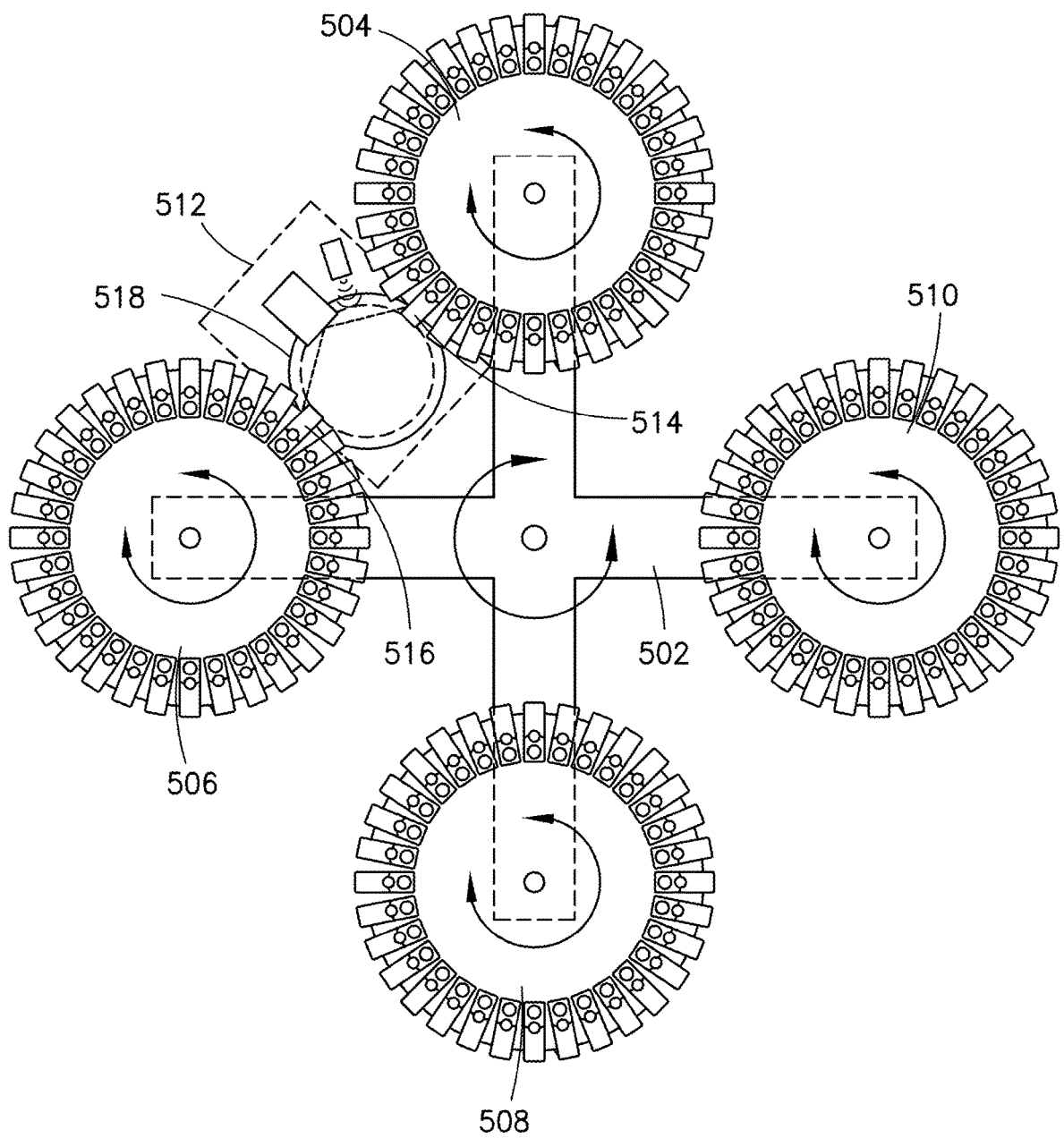
FIG. 5 is a top view of a four-carousel cartridge-based reagent disc dispensing system utilizing an X-shaped central turntable.
Figure 6A:
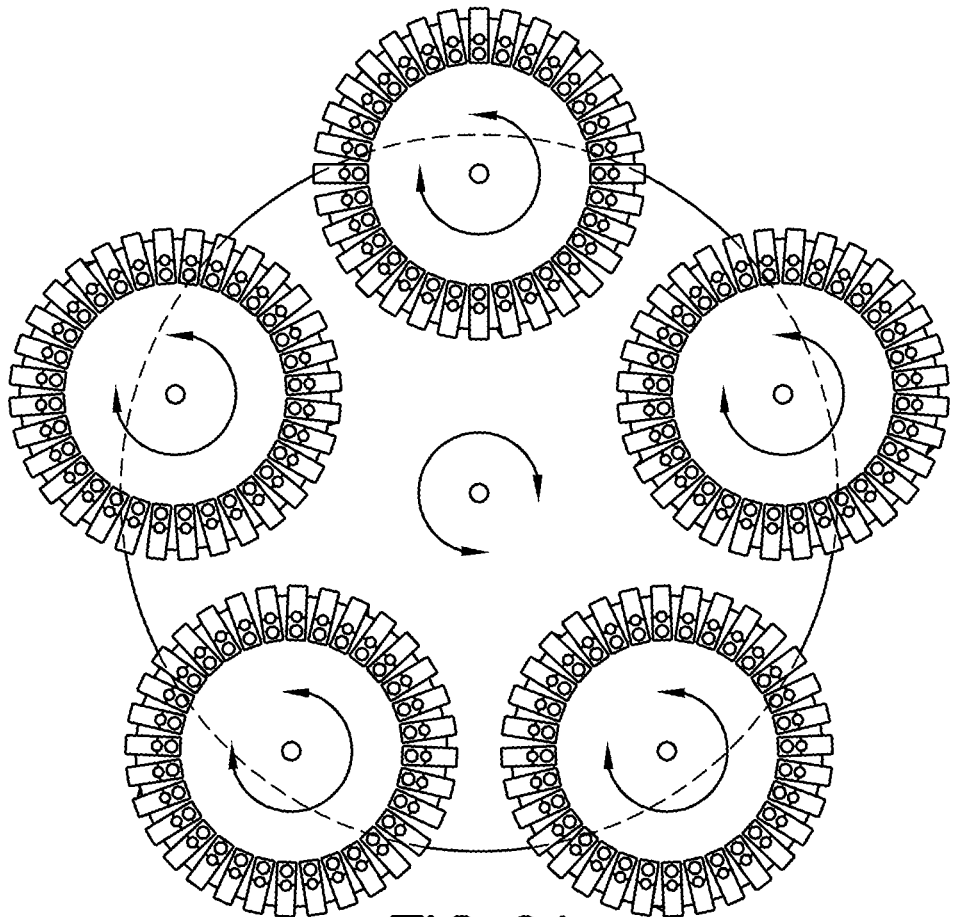
FIG. 6A is a top view of a five-carousel cartridge-based reagent disc dispensing system according to an alternate embodiment of the present invention
Figure 6B:
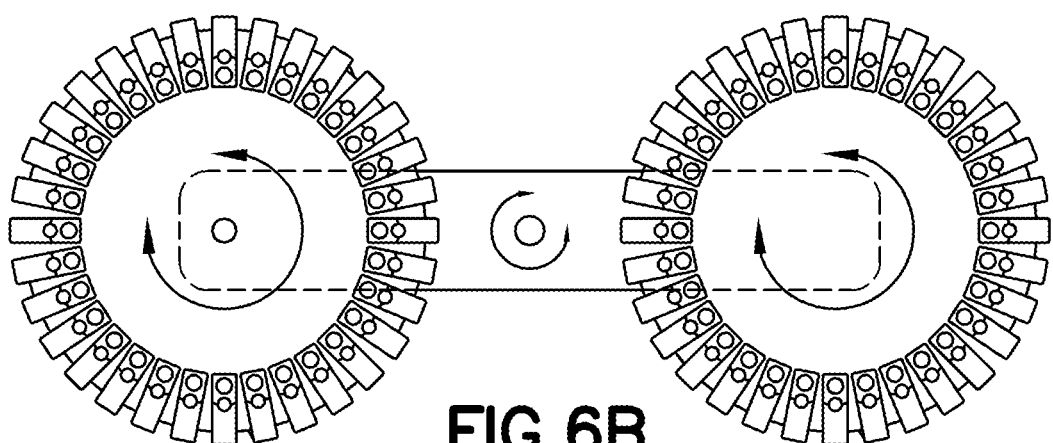
FIG. 6B is a top view of a two-carousel cartridge-based dispensing system according to an alternate embodiment of the present invention.

Different physical configurations, employing alternate central turntable geometries and differing numbers of mounted carousels can be implemented without departing from scope of the disclosed invention. For example, FIG. 5 shows X-shaped central turntable 502 having four mounted carousels (504, 506, 508 and 510). This X-shaped turntable operates in the same manner as the circular turntable system described in detail above. However, the configuration permits for the placement of loading station 512 so that a reagent disc from dispenser 514 (mounted upon carousel 504) and a reagent disc from dispenser 516 (mounted upon carousel 506) can be simultaneously dispensed into the surface of the medium in plate 518. Such simultaneous dispensing may require multiple composite cams, and would require the system to control the placement of two reagent disc dispensing cartridges. One cartridge on each of the opposing carousels to achieve simultaneous dispensing of reagent discs in their respective target locations on the opposed culture plates 124. This dual dispensing capability would result in an increased throughput of plates within the dispensing system. Other turntable/carousel configurations in accordance with the invention are shown in FIG. 6A (a five-carousel configuration), and FIG. 6B (a two-carousel configuration).

Figure 7A:
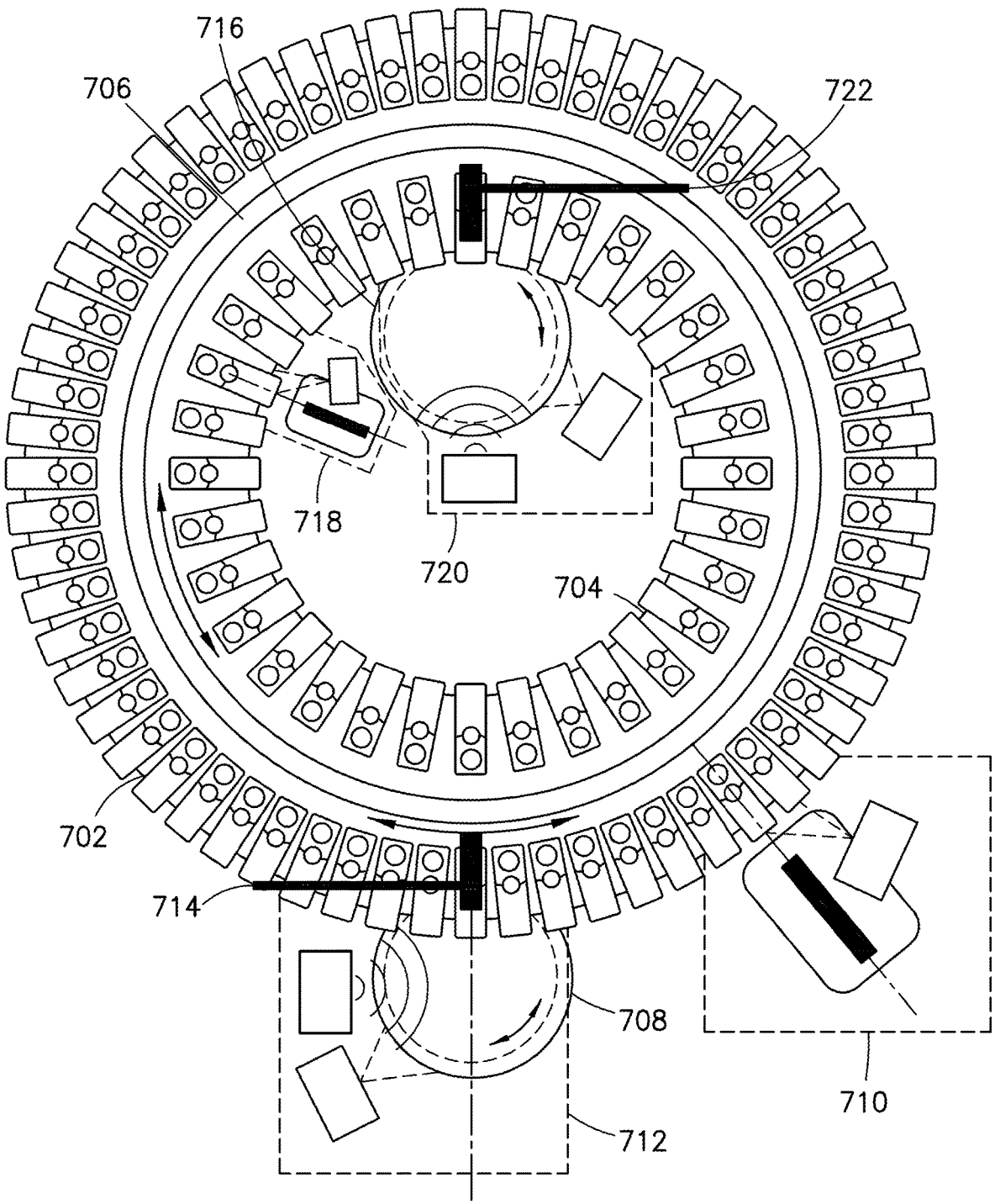
FIG. 7A is a top view of a concentric two-carousel cartridge-based dispensing system according to an alternate embodiment of the present invention.

FIG. 7A provides an illustration of yet another multiple-carousel embodiment of the invention. In this embodiment, two concentrically positioned carousels (702, 704) are rotatably mounted on a ring-shaped turntable (706). As in the previously described embodiments, these carousels can be independently rotated in response to command signals received from a control system. As shown, outer carousel 702 has 64 individual cartridges radially-mounted so as to permit reagent discs to be dispensed onto the surface of a medium contained in plate 708. This dispensing is performed in a manner identical to of previously described embodiments. Note that outer carousel 702 has an associated primer station (710), loading station (712) and composite cam arrangement (714); all of which operate in much the same manner as their analogous counterparts in previously described embodiments. Inner carousel 704 is shown to have 32 dispensers radially-mounted so as to permit reagent discs to be dispensed onto the surface of a medium contained in plate 716. Again, this dispensing is performed in a manner identical to of previously described embodiments, utilizing primer station 718, loading station 720 and composite cam arrangement 722.

Figure 7B:
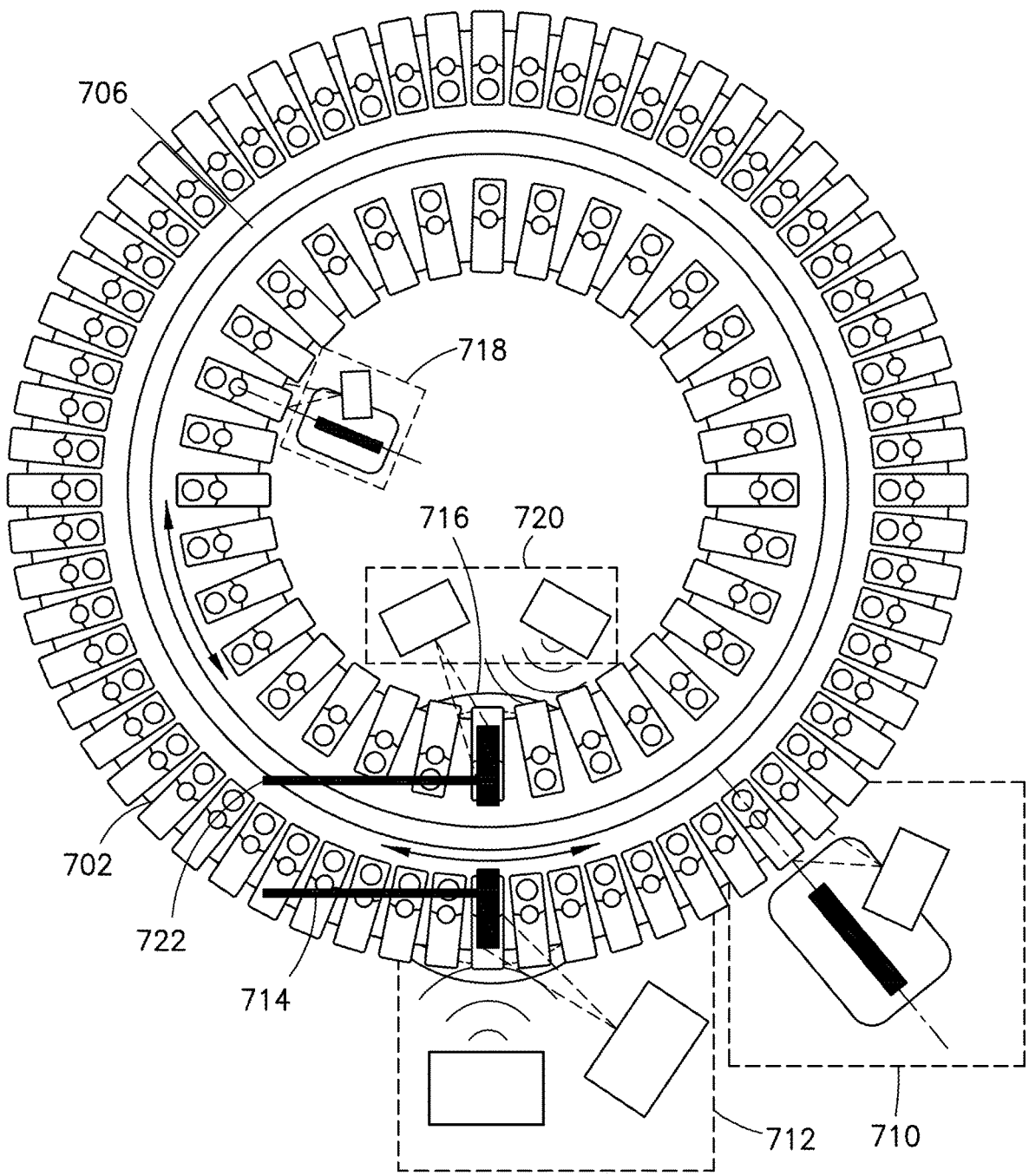
FIG. 7B is a top view of an alternate concentric two-carousel cartridge-based dispensing system according to the present invention.

An alternate concentric carousel embodiment is illustrated in FIG. 7B. As with the embodiment of FIG. 7A, the outer carousel 702 has an associated primer station (710), loading station (712) and composite cam arrangement (714), and the inner carousel 704 has primer station 718, loading station 720 and composite cam arrangement 722. Unlike the embodiment of FIG. 7A, this embodiment positions the dual carousels so that they straddle plate 716, permitting a disc to be deposited from the outer carousel and another disc to be deposited from the inner carousel. These discs would be on opposite ends of plate 716, separated by an angular distance of 180°. The discs could be deposited simultaneously or sequentially. This type of dispensing strategy would greatly cut throughput time of the system.

Additional sensors and controls may be included in the system. For example, a proximity sensor (such as ultrasonic proximity sensor 210) can be provided at each plate platform to sense the height of the surface of the medium contained within a given plate. This information could then be utilized by the system for multiple purposes. For example, the measurement would permit the sensing of a previously dispensed disc upon the medium surface. This would serve as a fail-safe to the system's internal tracking of dispensed disc placement upon the surface of the medium within an identified plate. If a disc was sensed in a location on a particular plate that was identified in the control system memory as unoccupied, or if the sensor failed to indicate the presence of a disc in particular location that was identified in the control system memory as occupied, the system would generate an error signal indicative of the apparent inconsistency. A technician or operator could then address the issue via a user interface.

The proximity sensor could also be utilized to provide a real-time quality check on the medium, so that prior to the introduction of a reagent tablet, the medium surface could be scanned for height/thickness consistency. A plate containing inferior media could be identified, removed from the system and replaced with an acceptable substitute prior to the dispensing of any reagent discs thereon. The proximity sensor could also be employed to permit the precise adjustment of the plate platform height. A hydraulic, pneumatic or electro-mechanical vertical platform height adjustment system, responsive to control signals from the microprocessor-based control system, could be implemented to precisely adjust the plate height as a function of the surface proximity measurement. The height adjustment would ensure that each dispensed disc would be implanted by the dispenser's vertical plunger to a precise, predetermined penetration into the surface of the medium. This assures that the reagent(s) contained within each disc would react consistently within a given plate, and from plate to plate.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A reagent dispensing system comprising:
a control system comprising a processor and a memory;
a rotatably mounted central turntable positionable in response to commands received from the control system;
a plurality of carousels, carried by and rotatably mounted upon the rotatably mounted central turntable, each positionable in response to command received from the control system; and
a plurality of dispenser cartridges, mounted about a circumference of each of the plurality of carousels carried by the rotatably mounted central turntable, wherein each of the plurality of dispenser cartridges comprises a reagent disc reservoir carrying reagent discs to be dispensed therefrom and a plunger assembly housing a vertical plunger;
a mechanical actuator positioned above a loading station wherein, when a dispenser cartridge is rotated into alignment with the actuator, a mechanical actuation of the dispenser cartridge results in dispensing of the reagent disc contained within the actuated dispenser cartridge by bringing the plunger assembly into proximity with a medium upon which the disc is to be dispensed prior to actuating the vertical plunger, wherein the medium is placed in the loading station, and whereby the reagent disc is dispensed onto a surface of a testing medium.

2. The reagent dispensing system of claim 1, wherein the mechanical actuator is configured to actuate at least one of the plurality of dispenser cartridges from a command received from the control system.

3. The reagent dispensing system of claim 1, wherein the reagent disc is dispensed via the vertical plunger of the dispenser cartridge.

4. The reagent dispensing system of claim 3, wherein the vertical plunger of the dispenser cartridge is actuated by a rotating cam of the mechanical actuator, wherein the rotating cam is responsive to a command received from the control system.

5. The reagent dispensing system of claim 4, wherein the plunger assembly is brought into proximity with a medium upon which the disc is to be dispensed prior to actuating the vertical plunger.

6. The reagent dispensing system of claim 1, wherein the testing medium is contained in a plate.

7. The reagent dispensing system of claim 1, further comprising a proximity sensor, in communication with the control system and adapted to scan and measure the surface of the testing medium.

8. The reagent dispensing system of claim 7, wherein the proximity sensor comprises an ultrasonic sensor.

9. The reagent dispensing system of claim 1, wherein each disc reservoir held in the dispenser cartridge has a machine-readable identification label affixed to it, and the system further comprising at least one optical sensor in communication with the control system and adapted to read the machine-readable identification labels, wherein the memory of the control system contains information associating each machine-readable label with at least one of: (a) a type of reagent contained within the dispenser cartridge having the machine-readable label, or (b) an amount of reagent available within the dispenser cartridge for dispensing.

10. The reagent dispensing system claim 9, wherein the machine-readable identification label comprises a barcode, and wherein the at least one optical sensor is a barcode reader.

11. The reagent dispensing system of claim 6, wherein the plate has a machine-readable identification label affixed to it, and further comprising at least one optical sensor in communication with the control system and adapted to read the machine-readable identification label, wherein the memory of the control system contains information associating the machine-readable identification label with at least one of: (a) a type of testing medium contained in the plate, (b) a type of reagent that has been dispensed onto the testing medium, (c) a location upon the testing medium at which reagents have been dispensed, (d) a type of any additional reagents dispensed onto the testing medium, or (e) the location upon the testing medium that is available for dispensing additional reagents thereon.

12. The reagent dispensing system claim 11, wherein the machine-readable identification label comprises a barcode, and wherein the at least one optical sensor is a barcode reader.

13. The reagent dispensing system of claim 1, wherein at least two of the carousels are mounted concentrically.

14. A method for automated dispensing of reagents in a system wherein the system comprises:
a control system comprising a processor and a memory;
a rotatably mounted central turntable positionable in response to commands received from the control system;
a plurality of carousels, carried by and rotatably mounted upon the rotatably mounted central turntable, each independently positionable in response to command received from the control system;
a plurality of dispenser cartridges, mounted about a circumference of each of the plurality of carousels, wherein each dispenser cartridge comprises a reagent disc reservoir carrying reagent discs to be dispensed therefrom and a vertical plunger;
a mechanical actuator positioned above a loading station;
wherein when a dispenser cartridge is rotated into alignment with the mechanical actuator, a mechanical actuation of a dispenser cartridge results in dispensing the reagent disc contained within the actuated dispenser cartridge; and
at least one test medium carried by a culture plate;

the method comprising:

positioning the rotatably mounted central turntable so as to place a selected carousel in a position proximate to the at least one test medium located in the loading station;

rotating a selected carousel to position a selected dispenser cartridge in a position to dispense the reagent disc on to the at least one test medium; and actuating the mechanical actuator to act upon the selected dispenser cartridge causing the reagent disc to be dispensed via the vertical plunger to dispense the reagent disc on to the test medium.

15. The method of claim 14, wherein a cam actuates the selected dispenser cartridge.

16. The method of claim 14, wherein the testing medium is contained in a plate.

17. The method of claim 14, further comprising the step of:
assessing a surface of the testing medium with a proximity sensor.

18. The method of claim 14, wherein each dispenser cartridge has a machine-readable identification label associated therewith, and the method further comprising:
reading the machine-readable identification label with an optical sensor; and
accessing data associated with the read machine-readable identification label from the memory of the control system; wherein the accessed data is indicative of at least one of: (a) a type of reagent contained within the dispenser cartridge having the machine-readable identification label affixed thereto, or (b) an amount of reagent available within the dispenser cartridge having the machine-readable identification label affixed thereto.

19. The method of claim 15, wherein the culture plate has a machine-readable identification label affixed to it, and the method further comprising:
reading said machine-readable identification label with an optical sensor; and
accessing data associated with the read label from the memory of the control system; wherein the accessed data is indicative of at least one of: (a) a type of test medium contained in the culture plate, (b) a type of reagent that has been dispensed onto the test medium, (c) a location upon the test medium at which reagents have been dispensed, (d) a type of additional reagents to be dispensed onto the test medium, or (e) optionally, the location upon the test medium that is available for the dispensing of additional reagents.

* * * * *